United States Patent
Jeon et al.

(10) Patent No.: US 11,490,859 B2
(45) Date of Patent: Nov. 8, 2022

(54) BIO-INSPIRED, HIGHLY STRETCHABLE AND CONDUCTIVE DRY ADHESIVE PATCH, METHOD OF MANUFACTURING THE SAME AND WEARABLE DEVICE INCLUDING THE SAME

(71) Applicant: Korea Advanced Institute of Science and Technology, Daejeon (KR)

(72) Inventors: Seok-woo Jeon, Daejeon (KR); Tae-Hoon Kim, Daejeon (KR); Dong-hwi Cho, Daejeon (KR); Junyong Park, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 664 days.

(21) Appl. No.: 16/486,245

(22) PCT Filed: Feb. 5, 2018

(86) PCT No.: PCT/KR2018/001510
§ 371 (c)(1),
(2) Date: Aug. 15, 2019

(87) PCT Pub. No.: WO2018/151448
PCT Pub. Date: Aug. 23, 2018

(65) Prior Publication Data
US 2020/0337640 A1    Oct. 29, 2020

(30) Foreign Application Priority Data
Feb. 16, 2017 (KR) .......................... 10-2017-0021111

(51) Int. Cl.
*G08B 21/04*    (2006.01)
*A61B 5/00*    (2006.01)
(Continued)

(52) U.S. Cl.
CPC .............. *A61B 5/6833* (2013.01); *A61B 5/25* (2021.01); *H01L 21/56* (2013.01); *H01L 21/768* (2013.01); *H01L 2021/60277* (2013.01)

(58) Field of Classification Search
USPC ......... 340/539.12, 539.18, 539.24, 634, 647, 340/691.2, 691.6, 5.52, 7.26, 384.3
See application file for complete search history.

(56) References Cited

U.S. PATENT DOCUMENTS 3,916,488 A * 11/1975 Gazda ................... B29C 48/151
                                                            24/20 LS
8,168,692 B2 * 5/2012 Wenz .................... A61L 27/446
                                                            606/94
(Continued)

FOREIGN PATENT DOCUMENTS

KR    10-1025696 B1    3/2011
KR    2015-0030403 A    3/2015
(Continued)

OTHER PUBLICATIONS

PCT International Search Report dated Jun. 26, 2018 for International Application No. PCT/KR2018/001510; 4 Pages.
(Continued)

*Primary Examiner* — Daniel Previl
(74) *Attorney, Agent, or Firm* — Daly Crowley Mofford & Durkee, LLP

(57) ABSTRACT

In a method of manufacturing a biomimetic highly stretchable conductive dry adhesive patch, a mold including a plurality of holes is provided by etching a semiconductor substrate including an insulation layer based on a footing effect. A conductive polymer composite is provided by dispersing mixed conductive fillers in a liquid elastomer. The mixed conductive fillers are formed by mixing one-dimensional conductive fillers and two-dimensional conductive fillers. The conductive polymer composite is applied on (Continued)

the mold such that the conductive polymer composite is injected into the plurality of holes. A conductive dry adhesive structure including a plurality of micropillars corresponding to the plurality of holes is obtained by performing a post-treatment on the conductive polymer composite applied on the mold and by removing the mold. Each of the plurality of micropillars includes a body portion and a tip portion. The tip portion has a spatula shape, is formed on the body portion, and has an area larger than that of the body portion in a plan view.

14 Claims, 23 Drawing Sheets

(51) Int. Cl.
    *H01L 21/56* (2006.01)
    *H01L 21/768* (2006.01)
    *A61B 5/25* (2021.01)
    *H01L 21/60* (2006.01)

(56) References Cited

U.S. PATENT DOCUMENTS

| | | | | |
|---|---|---|---|---|
| 8,176,782 | B2* | 5/2012 | Furukubo | G01P 15/125 73/514.32 |
| 8,703,032 | B2* | 4/2014 | Menon | C09J 7/00 264/318 |
| 10,037,098 | B2* | 7/2018 | Bao | G06F 3/04144 |
| 10,130,736 | B1* | 11/2018 | Semler | A61L 27/3691 |
| 10,156,560 | B1* | 12/2018 | Bashir | G01N 33/5029 |
| 2004/0241417 | A1* | 12/2004 | Fischer | C09J 11/04 428/317.9 |
| 2005/0236407 | A1* | 10/2005 | Aisenbrey | H01Q 9/0407 219/730 |
| 2015/0329743 | A1* | 11/2015 | Lu | C09J 7/00 428/196 |
| 2017/0312385 | A1* | 11/2017 | Ahn | A61P 19/08 |
| 2019/0298885 | A1* | 10/2019 | Schilling | A61L 27/3839 |
| 2020/0181455 | A1* | 6/2020 | Ahn | A61L 27/34 |

FOREIGN PATENT DOCUMENTS

| | | |
|---|---|---|
| KR | 10-1533403 B1 | 7/2015 |
| KR | 2016-0047184 A | 5/2016 |
| KR | 2016-0064815 A | 6/2016 |

OTHER PUBLICATIONS

Naver News, "Measurement of Biometric Information with a Conductive Adhesive Pad Obtained by Replicating a Gecko;" English Abstract Only; Yonhapnews; Published Feb. 16, 2017; 10 Pages.

\* cited by examiner

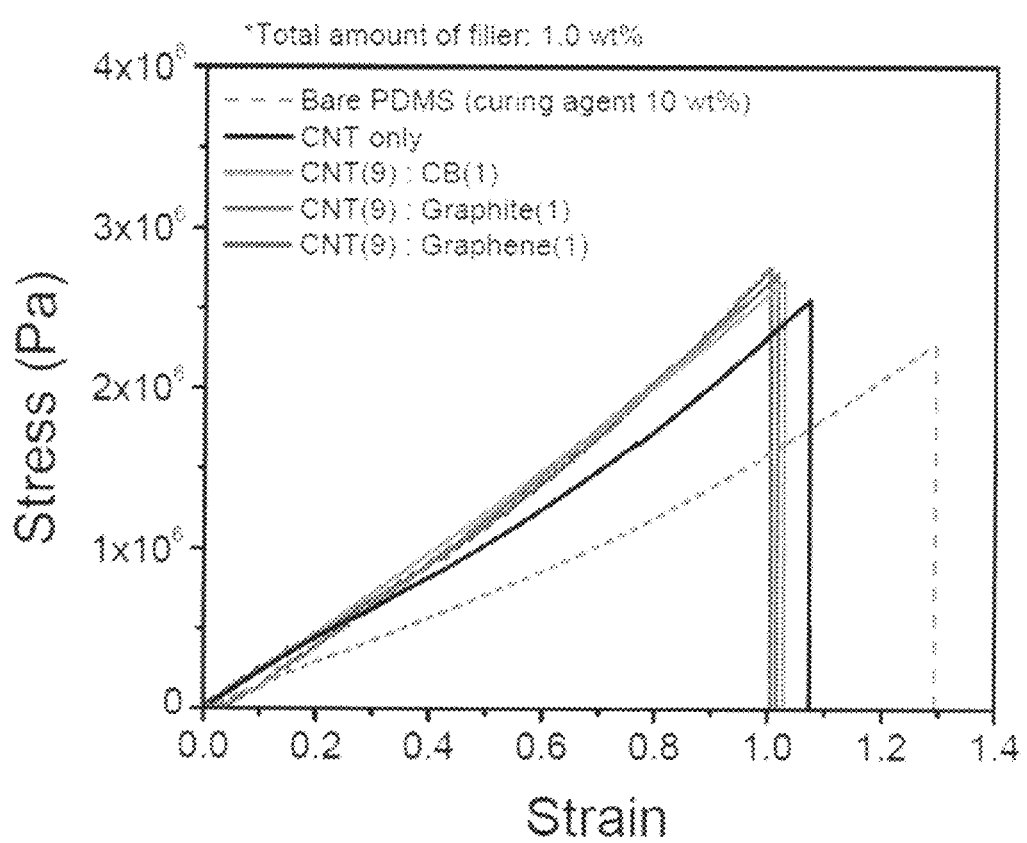

FIG. 21A
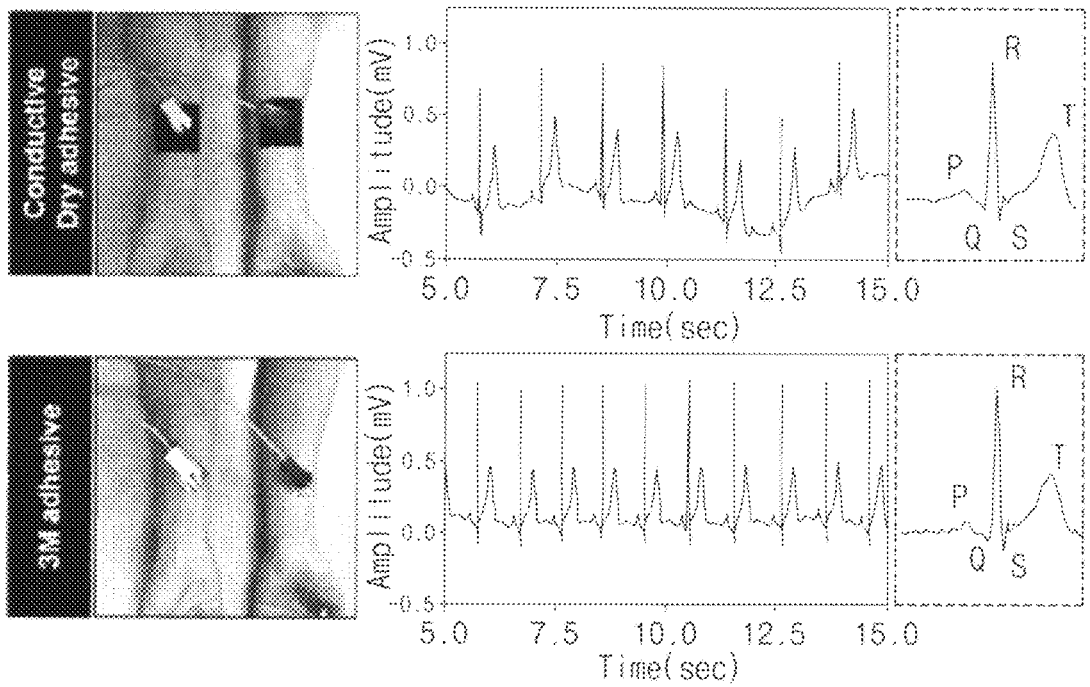
FIG. 21B
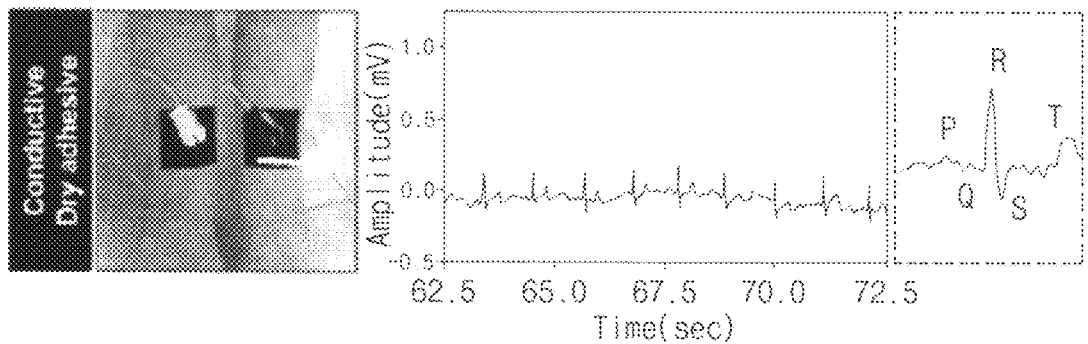
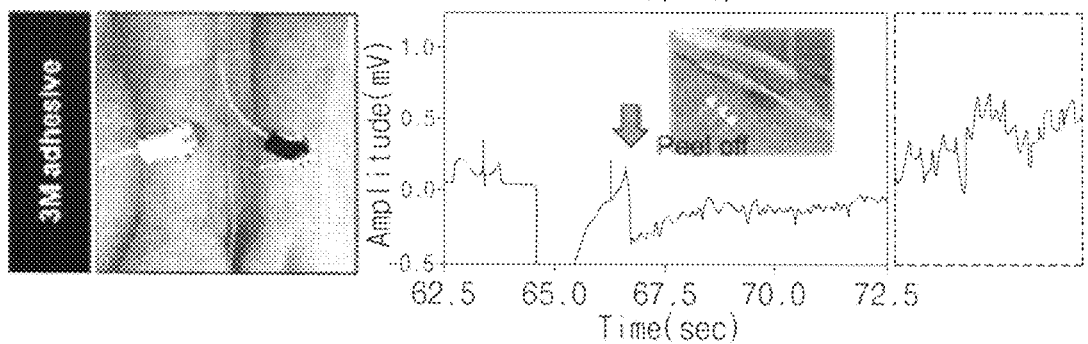

BIO-INSPIRED, HIGHLY STRETCHABLE AND CONDUCTIVE DRY ADHESIVE PATCH, METHOD OF MANUFACTURING THE SAME AND WEARABLE DEVICE INCLUDING THE SAME

CROSS-REFERENCE TO RELATED APPLICATION

This application is a U.S. National Stage of PCT/KR2018/001510 filed in the Korean language on Feb. 5, 2018, entitled "DRY-TYPE BIOMIMETIC ADHESION PATCH HAVING HIGH ELASTICITY AND CONDUCTIVITY, METHOD FOR MANUFACTURING SAME, AND WEARABLE DEVICE COMPRISING SAME," which application claims the priority benefit of Korean Patent Application No. 10-2017-0021111 filed on Feb. 16, 2017 in the Korean Intellectual Property Office, the disclosure of which is incorporated herein by reference.

BACKGROUND

1. Technical Field

Example embodiments relate generally to conductive adhesive patches, and more particularly to biomimetic highly stretchable conductive dry adhesive patches, methods of manufacturing the biomimetic highly stretchable conductive dry adhesive patches, and wearable devices including the biomimetic highly stretchable conductive dry adhesive patches.

2. Description of the Related Art

Recently, various wearable platform technologies using conductive adhesive patches that can be attached to the user's body, such as health rehabilitation treatment, personal health monitoring and athlete performance monitoring, have been studied, and thus researches have been actively conducted on materials that are flexible, stretchable and excellent in electrical conductivity. To be used as conductive adhesive patches, not only flexibility, elasticity and electrical conductivity but also excellent adhesive properties and adhesive durability are required. Materials and/or structures with excellent flexibility, elasticity and electrical conductivity and materials and/or structures with excellent adhesive properties and adhesive durability have been studied separately, however, there has been a problem that it is difficult to implement materials and/or structures and conductive adhesive patches using the same that can satisfy all the above characteristics at the same time.

SUMMARY

Some example embodiments provide a method of manufacturing a biomimetic highly stretchable conductive dry adhesive patch capable of having improved characteristics.

Some example embodiments provide a biomimetic highly stretchable conductive dry adhesive patch obtained by the method.

Some example embodiments provide a wearable device including the biomimetic highly stretchable conductive dry adhesive patch.

According to example embodiments, in a method of manufacturing a biomimetic highly stretchable conductive dry adhesive patch, a mold including a plurality of holes is provided by etching a semiconductor substrate including an insulation layer based on a footing effect. A conductive polymer composite is provided by dispersing mixed conductive fillers in a liquid elastomer. The mixed conductive fillers are formed by mixing one-dimensional conductive fillers and two-dimensional conductive fillers. The conductive polymer composite is applied on the mold such that the conductive polymer composite is injected into the plurality of holes. A conductive dry adhesive structure including a plurality of micropillars corresponding to the plurality of holes is obtained by performing a post-treatment on the conductive polymer composite applied on the mold and by removing the mold. Each of the plurality of micropillars includes a body portion and a tip portion. The tip portion has a spatula shape, is formed on the body portion, and has an area larger than that of the body portion in a plan view.

In some example embodiments, an amount of the one-dimensional conductive fillers included in the mixed conductive fillers may be greater than an amount of the two-dimensional conductive fillers included in the mixed conductive fillers.

In some example embodiments, a ratio of the one-dimensional conductive fillers and the two-dimensional conductive fillers in the mixed conductive fillers may be within a range of about 8:2 to about 9.99:0.01.

In some example embodiments, an amount of the mixed conductive fillers dispersed in the liquid elastomer may be less than or equal to about 1.0 weight percent (wt %) based on a total weight of the conductive polymer composite.

In some example embodiments, an aspect ratio obtained by dividing a height of each of the plurality of micropillars by a width of each of the plurality of micropillars may be within a range of about 2 to about 4.

In some example embodiments, each of the body portion and the tip portion may have a cylindrical shape. The body portion may be formed on an elastic substrate including the conductive polymer composite, and may have a first diameter and a first thickness. The tip portion may be formed on the body portion, and may have a second diameter larger than the first diameter and a second thickness smaller than the first thickness.

In some example embodiments, each of the one-dimensional conductive fillers and the two-dimensional conductive fillers may include a carbon-based nanoconductive material.

In some example embodiments, the one-dimensional conductive fillers may include a conductive material based on carbon nanotube (CNT).

In some example embodiments, the two-dimensional conductive fillers may include a conductive material based on a material selected from the group consisting of graphene, carbon black (CB) and graphite.

In some example embodiments, the one-dimensional conductive fillers may include a conductive material based on silver nanowire.

In some example embodiments, the liquid elastomer may include a material selected from the group consisting of polydimethylsiloxane (PDMS), PDMS modified urethane acrylate (PUA), perfluoropolyether (PFPE) and polyethylene (PE).

In some example embodiments, when providing the mold, a photoresist layer may be formed on the semiconductor substrate. The semiconductor substrate may include a bare semiconductor wafer, the insulation layer formed on the bare semiconductor wafer, and a semiconductor layer formed on the insulation layer. A photoresist pattern including a hole array may be formed by patterning the photoresist layer. An etching process may be performed on the semiconductor layer using the photoresist pattern as a mask until the insulation layer is exposed. The photoresist pattern may be removed. A surface treatment may be performed on the mold.

In some example embodiments, each of the plurality of holes may include a first portion and a second portion. The first portion may be formed adjacent to the insulation layer, and may have a shape corresponding to the tip portion. The second portion may be formed on the first portion, and may have a shape corresponding to the body portion. A width and a thickness of the first portion may be determined based on an execution time during which the etching process is performed on the semiconductor layer.

According to example embodiments, a biomimetic highly stretchable conductive dry adhesive patch includes an elastic structure and mixed conductive fillers. The elastic structure is formed of an elastic material, and includes an elastic substrate and a plurality of micropillars formed on the elastic substrate. The mixed conductive fillers are formed by mixing one-dimensional conductive fillers and two-dimensional conductive fillers, and are dispersed in the elastic structure to form a conductive network. Each of the plurality of micropillars includes a body portion and a tip portion. The tip portion has a spatula shape, is formed on the body portion, and has an area larger than that of the body portion in a plan view. A conductive dry adhesive structure is formed by the elastic structure and the mixed conductive fillers.

In some example embodiments, an amount of the one-dimensional conductive fillers included in the mixed conductive fillers may be greater than an amount of the two-dimensional conductive fillers included in the mixed conductive fillers.

In some example embodiments, a ratio of the one-dimensional conductive fillers and the two-dimensional conductive fillers in the mixed conductive fillers may be within a range of about 8:2 to about 9.99:0.01.

In some example embodiments, an amount of the mixed conductive fillers dispersed in the elastic structure may be less than or equal to about 1.0 weight percent (wt %) based on a total weight of the elastic structure and the mixed conductive fillers.

In some example embodiments, an aspect ratio obtained by dividing a height of each of the plurality of micropillars by a width of each of the plurality of micropillars may be within a range of about 2 to about 4.

In some example embodiments, each of the one-dimensional conductive fillers and the two-dimensional conductive fillers may include a carbon-based nanoconductive material. The one-dimensional conductive fillers may include a conductive material based on carbon nanotube (CNT). The two-dimensional conductive fillers may include a conductive material based on a material selected from the group consisting of graphene, carbon black (CB) and graphite.

According to example embodiments, a wearable device includes a biomimetic highly stretchable conductive dry adhesive patch, a measurer and a processor. The measurer is connected to the biomimetic highly stretchable conductive dry adhesive patch. The processor performs a predetermined data processing operation based on an output of the measurer. The biomimetic highly stretchable conductive dry adhesive patch includes an elastic structure and mixed conductive fillers. The elastic structure is formed of an elastic material, and includes an elastic substrate and a plurality of micropillars formed on the elastic substrate. The mixed conductive fillers are formed by mixing one-dimensional conductive fillers and two-dimensional conductive fillers, and are dispersed in the elastic structure to form a conductive network. Each of the plurality of micropillars includes a body portion and a tip portion. The tip portion has a spatula shape, is formed on the body portion, and has an area larger than that of the body portion in a plan view. A conductive dry adhesive structure is formed by the elastic structure and the mixed conductive fillers.

As described above, the biomimetic highly stretchable conductive dry adhesive patch according to example embodiments may include the elastic structure that includes mushroom-shaped micropillars formed by replicating the numerous cilia structures that exist on the sole of the gecko lizard, and the conductive network may be formed by dispersing the mixed conductive fillers that are formed by mixing the one-dimensional conductive fillers and the two-dimensional conductive fillers in the elastic structure. Thus, the biomimetic highly stretchable conductive dry adhesive patch may adhere to the skin by the physical force of the mushroom-shaped micropillars without extra chemical adhesive, so it does not give the user a feeling of irritation or foreign objects. Instead of separately forming a metal electrode and an adhesive, the elastic structure may simultaneously perform a role of the electrode having the electrical conductivity and the adhesive having the adhesion force, the biomimetic highly stretchable conductive dry adhesive patch may be implemented in a fairly simple all-in-one structure.

In the biomimetic highly stretchable conductive dry adhesive patch according to example embodiments, the elastic structure may be manufactured using a rubber or elastic material having excellent elasticity and/or flexibility, the mushroom-shaped micropillars may have a relatively high aspect ratio, and thus it may be conformally attached to the skin having invisible roughness. In addition, due to the hydrophobicity of the rubber material and the micropillars, the dusts adhering to the surface by repeated uses may be removed by exposing the biomimetic highly stretchable conductive dry adhesive patch to running water, and thus it may be used semi-permanently.

BRIEF DESCRIPTION OF THE DRAWINGS

FIGS. 13A, 13B, 14, 15A, 15B, 16A and 16B are diagrams for describing the electrical conductivity and flexibility/elasticity according to a type of mixed conductive fillers included in a biomimetic highly stretchable conductive dry adhesive patch according to example embodiments.

FIGS. 21A, 21B, 21C, 21D and 21E are diagrams illustrating examples of using a biomimetic highly stretchable conductive dry adhesive patch according to example embodiments as an electrocardiogram measurer.

DETAILED DESCRIPTION OF THE EMBODIMENTS

Figure 1:
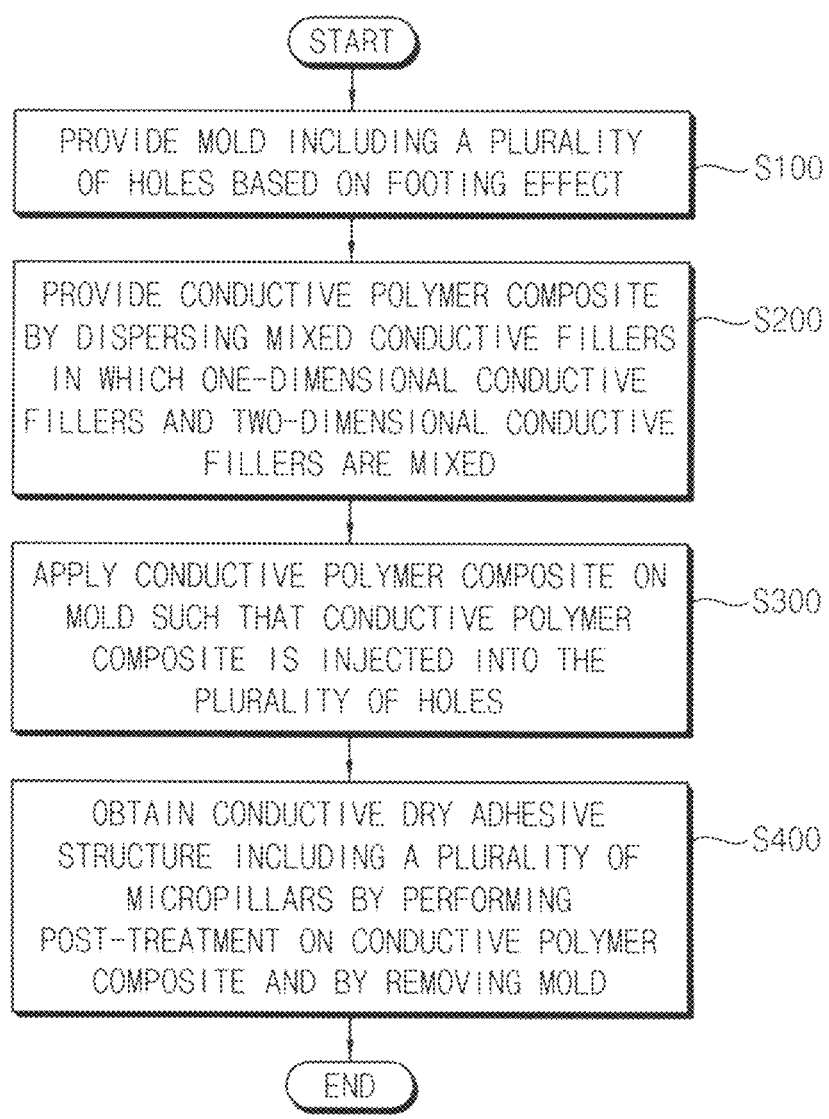
FIG. 1 is a flowchart illustrating a method of manufacturing a biomimetic highly stretchable conductive dry adhesive patch according to example embodiments.

Various example embodiments will be described more fully with reference to the accompanying drawings, in which embodiments are shown. This inventive concept may, however, be embodied in many different forms and should not be construed as limited to the embodiments set forth herein.

Rather, these embodiments are provided so that this disclosure will be thorough and complete, and will fully convey the scope of the inventive concept to those skilled in the art. Like reference numerals refer to like elements throughout this application.

It will be understood that, although the terms first, second, etc. may be used herein to describe various elements, these elements should not be limited by these terms. These terms are used to distinguish one element from another. For example, a first element could be termed a second element, and, similarly, a second element could be termed a first element, without departing from the scope of the inventive concept. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments and is not intended to be limiting of the inventive concept. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

If a particular embodiment is otherwise feasible, the functions or operations specified in a particular block may occur differently from the order specified in the flowchart. For example, two consecutive blocks may actually be performed at substantially the same time, and the blocks may be performed backwards depending on the associated function or operation.

The above and other features of the inventive concept will become more apparent by describing in detail example embodiments thereof with reference to the accompanying drawings. The same reference numerals are used for the same elements in the drawings and redundant explanations for the same elements are omitted.

FIG. 1 is a flowchart illustrating a method of manufacturing a biomimetic highly stretchable conductive dry adhesive patch according to example embodiments.

Referring to FIG. 1, in a method of manufacturing a biomimetic highly stretchable conductive dry adhesive patch according to example embodiments, a mold including a plurality of holes is provided by etching a semiconductor substrate including an insulation layer based on a footing effect (step S100). Step S100 will be described with reference to FIGS. 2 and 3.

A conductive polymer composite is provided by dispersing mixed conductive fillers in a liquid elastomer (step S200). The mixed conductive fillers are formed by mixing one-dimensional (1D) conductive fillers and two-dimensional (2D) conductive fillers. The one-dimensional conductive fillers may be or include a conductive material in an one-dimensional form such as a line, and the two-dimensional conductive fillers may be or include a conductive material in a two-dimensional form such as a face (or side), surface, a lump and/or a chunk. For example, each of the one-dimensional conductive fillers and the two-dimensional conductive fillers may include a carbon-based nanoconductive material. In other words, the conductive polymer composite may include a one-dimensional and two-dimensional (1D-2D) hybrid carbon nanofillers. For example, the liquid elastomer may include polydimethylsiloxane (PDMS).

The conductive polymer composite is applied or spread on the mold such that the conductive polymer composite is injected into the plurality of holes (step S300). A conductive dry adhesive structure including a plurality of micropillars corresponding to the plurality of holes is obtained by performing a post-treatment or a post-processing on the conductive polymer composite applied or spread on the mold and by removing the mold (step S400).

Each of the plurality of micropillars includes a body portion and a tip portion having a spatula shape. The tip portion is formed on the body portion, and having an area larger than that of the body portion in a plan view. In other words, each micropillar may be formed to include the body portion which has a predetermined width and the tip portion which is formed at an end of the body portion and has a larger width than the body portion. Such structure may be referred to as a mushroom-shaped (or mushroom-like) structure.

The plurality of micropillars included in the conductive dry adhesive structure for implementing the biomimetic highly stretchable conductive dry adhesive patch according to example embodiments may be formed by replicating, simulating, imitating, or copying the numerous cilia or ciliated structures that exist on a sole of a gecko lizard. To implement such gecko-inspired or gecko-like structure, the mold including the plurality of holes corresponding to a reverse structure (or a reverse-phase structure) of the cilia structures may be fabricated, and the plurality of micropillars corresponding to the cilia structures may be fabricated using the mold. Thus, each of the plurality of holes may have the mushroom-shaped structure corresponding to a reverse structure of each of the plurality of micropillars.

Figure 2:
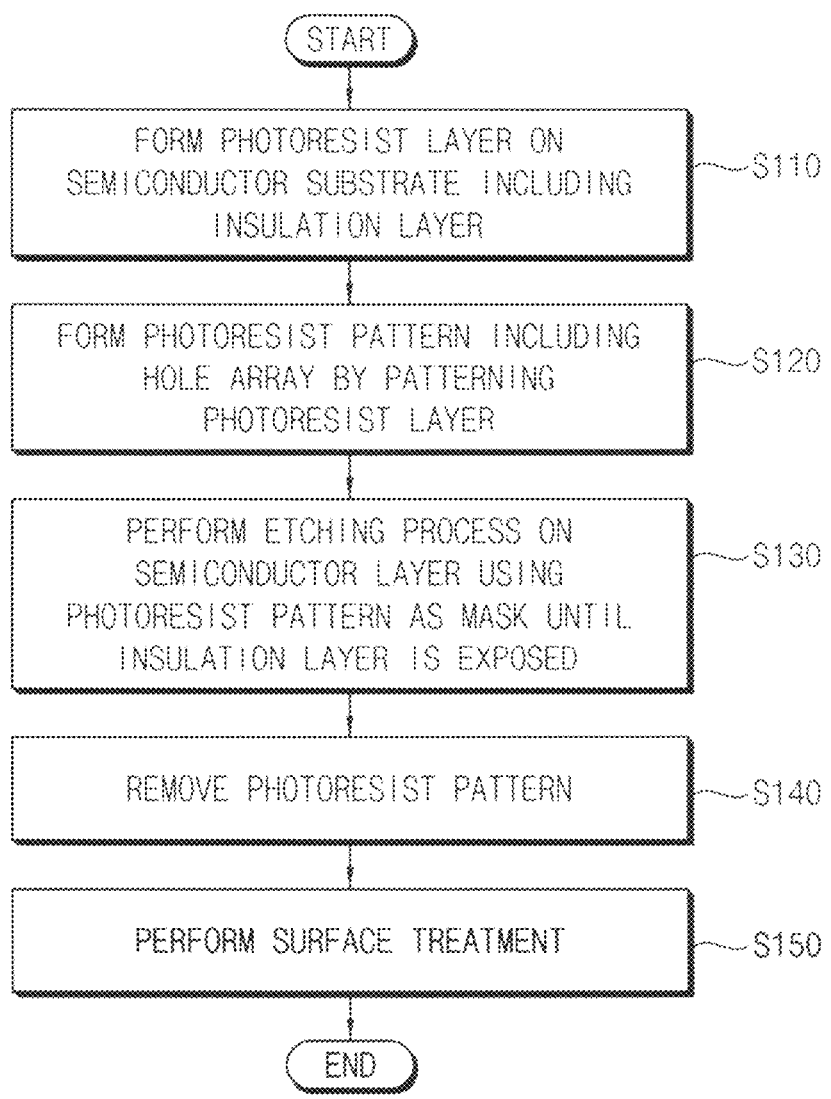
FIGS. 2 and 3 are diagrams for describing an operation of providing a mold including a plurality of holes in FIG. 1.
Figure 3:
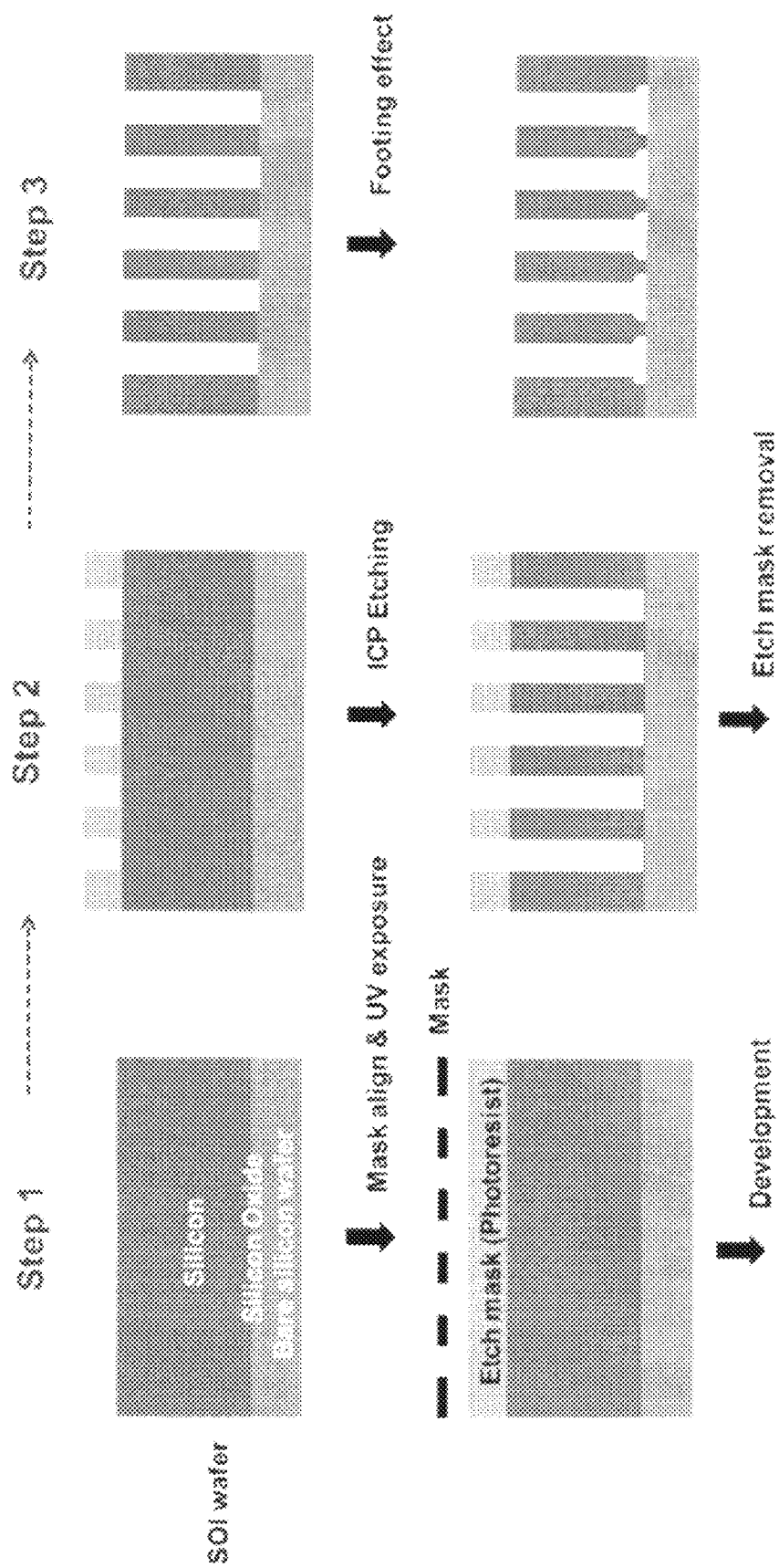

FIGS. 2 and 3 are diagrams for describing an operation of providing a mold including a plurality of holes in FIG. 1. FIG. 2 is a flowchart illustrating an example of step S100 in FIG. 1. FIG. 3 are cross-sectional views for describing a plurality of steps in FIG. 2.

Referring to FIGS. 2 and 3, when providing the mold including the plurality of holes (step S100 in FIG. 1), a photoresist layer may be formed on the semiconductor substrate including the insulation layer (step S110). The semiconductor substrate may include a bare semiconductor wafer, the insulation layer formed on the bare semiconductor wafer, and a semiconductor layer formed on the insulation layer. For example, as illustrated in an upper cross-sectional view of Step 1 in FIG. 3, the semiconductor substrate may be a silicon on insulator (SOI) substrate including a bare silicon wafer, a silicon oxide and a silicon layer. As illustrated in a lower cross-sectional view of Step 1 in FIG. 3, the photoresist layer may be formed on the semiconductor substrate.

In some example embodiments, the photoresist layer may be formed by applying or spreading a photoresist material of negative type or tone on the semiconductor substrate by a spin coating process. In some example embodiments, a pre-treatment or a pre-processing may be performed on the semiconductor substrate before the photoresist layer is formed on the semiconductor substrate.

A photoresist pattern including a hole array may be formed by patterning the photoresist layer (step S120). For example, as illustrated in the lower cross-sectional view of Step 1 in FIG. 3, a mask having a pattern corresponding to the hole array may be disposed on the semiconductor substrate on which the photoresist layer is formed (e.g., Mask align in FIG. 3), and an ultraviolet laser may be irradiated on the mask and the semiconductor substrate to perform an exposure process (e.g., UV exposure in FIG. 3). After the exposure process, the photoresist layer may be developed (e.g., Development in FIG. 3), and thus the photoresist pattern including the hole array may be formed as illustrated in an upper cross-sectional view of Step 2 in FIG. 3.

In some example embodiments, the plurality of holes (e.g., the plurality of mushroom-shaped holes) included in the mold and a plurality of second holes that correspond to the plurality of mushroom-shaped holes and are included in the hole array may be uniformly and regularly arranged. For example, as will be described with reference to FIGS. 5 and 6, the mushroom-shaped holes in the mold and the plurality of second holes in the hole array may be arranged in a matrix formation.

An etching process may be performed on the semiconductor layer using the photoresist pattern as a mask until the insulation layer is exposed (step S130). For example, as illustrated in a lower cross-sectional view of Step 2 and an upper cross-sectional view of Step 3 in FIG. 3, the etching process may be performed on the semiconductor layer until the insulation layer is exposed, and then the insulation layer may operate as an etch stopper. When the etching process is excessively performed even after the insulation layer is exposed, the footing effect may occur in which a lower portion of the semiconductor layer adjacent to the insulation layer is excessively etched (e.g., an end portion of the semiconductor layer which is a portion adjacent to the etch stopper may be etched slightly horizontally rather than vertically). As a result, as illustrated in a lower cross-sectional view of Step 3 in FIG. 3, the plurality of mushroom-shaped holes may be formed.

In some example embodiments, the etching process may be a dry etching process. For example, deep reactive ion etching (DRIE), which is a type of the dry etching process, may be performed in step S130. For example, inductively coupled plasma (ICP) etching may be performed.

In some example embodiments, each of the plurality of holes (e.g., each of the plurality of mushroom-shaped holes) may include a first portion which is a lower portion and a second portion which is an upper portion. The first portion may be formed adjacent to the insulation layer, and may have a shape corresponding to the tip portion of each micropillar. The second portion may be formed on the first portion, and may have a shape corresponding to the body portion of each micropillar. A width and a thickness of the first portion may be determined based on an execution time during which the etching process is performed on the semiconductor layer.

The photoresist pattern may be removed (step S140), and thus the mold including the plurality of holes may be obtained. For example, organic solvents may be used for removing the photoresist pattern (e.g., Etch mask removal in FIG. 3).

A surface treatment may be performed on the mold from which the photoresist pattern is removed (step S150). The interfacial energy of the mold including the plurality of holes may be reduced by the surface treatment, and thus the removal of the mold may be easier in step S400 of FIG. 1. For example, fluoro-based surface treatment solutions may be used to coat a surface of the mold by self assembly monolayer (SAM) method. Since the mold, which is thinly coated with fluorine based solutions, has a relatively low interfacial energy, the plurality of micropillars in the conductive dry adhesive structure may be obtained with more reproducibly and without damage and/or defects when the mold is removed.

Figure 4:
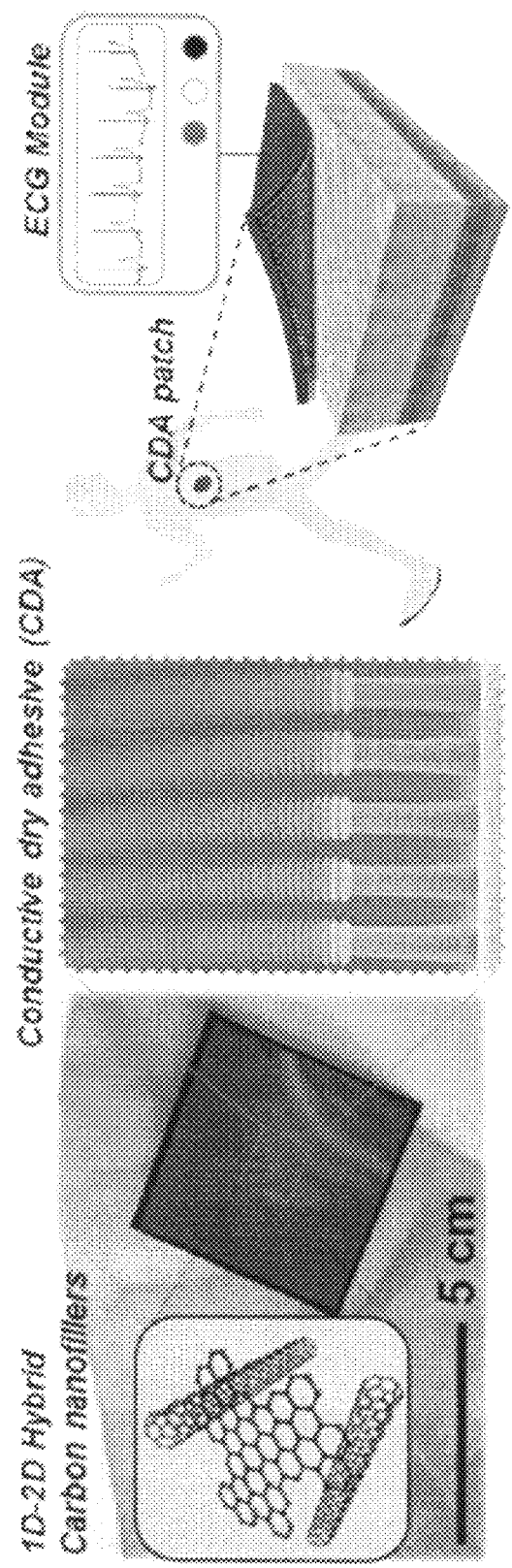
FIG. 4 is a diagram illustrating a biomimetic highly stretchable conductive dry adhesive patch according to example embodiments.

FIG. 4 is a diagram illustrating a biomimetic highly stretchable conductive dry adhesive patch according to example embodiments.

Referring to FIG. 4, a biomimetic highly stretchable conductive dry adhesive patch according to example embodiments includes an elastic (or elastomeric) structure and mixed conductive fillers. A conductive dry adhesive structure (or simply a conductive dry adhesive (CDA)) is formed or implemented by the elastic structure and the mixed conductive fillers.

The elastic structure is formed of an elastic material, and includes an elastic substrate and a plurality of micropillars formed on the elastic substrate. For example, as with the plurality of holes included in the mold, the plurality of micropillars may be uniformly and regularly arranged and may be arranged in a matrix formation.

Each of the plurality of micropillars includes a body portion (or a stem structure) and a tip portion (or a tip structure). The body portion is formed on the elastic substrate. The tip portion is formed on the body portion, and has an area larger than that of the body portion in a plan view. The body portion and the tip portion may correspond to the second portion and the first portion of each of the plurality of holes included in the mold, respectively.

In some example embodiments, each of the body portion and the tip portion may have a cylindrical shape. For example, the body portion may have a first diameter and a first thickness, and the tip portion may have a second diameter larger than the first diameter and a second thickness smaller than the first thickness. In addition, the first portion of each of the plurality of holes may have a third diameter and a third thickness, and the second portion of each of the plurality of holes may have a fourth diameter smaller than the third diameter and a fourth thickness larger than the third thickness. The third diameter and the third thickness may be substantially the same as the second diameter and the second thickness, respectively, and the fourth diameter and the fourth thickness may be substantially the same as the first diameter and the first thickness.

As described with reference to FIG. 1, the elastic structure may be obtained by performing the post-treatment on the liquid elastomer in which the mixed conductive fillers are dispersed (e.g., by performing the post-treatment on the conductive polymer composite). For example, the liquid elastomer may include a material based on polydimethylsiloxane (PDMS). However, the liquid elastomer is not limited thereto. For example, the liquid elastomer may include a material selected from the group consisting of PDMS modified urethane acrylate (PUA), perfluoropolyether (PFPE) and polyethylene (PE). In other words, the liquid elastomer may include any liquid polymer elastic material.

The mixed conductive fillers are formed by mixing one-dimensional conductive fillers and two-dimensional conductive fillers. The mixed conductive fillers are dispersed in the elastic structure to form a conductive network (e.g., percolated conductive nano-network), which is an 1D-2D hybrid conductive network.

As described with reference to FIG. 1, each of the one-dimensional conductive fillers and the two-dimensional conductive fillers may include a carbon-based nanoconductive material. For example, the one-dimensional conductive fillers may include a conductive material based on carbon nanotube (CNT), and the two-dimensional conductive fillers may include a conductive material based on a material selected from the group consisting of graphene, carbon black (CB) and graphite. However, the one-dimensional conductive fillers and the two-dimensional conductive fillers are not limited thereto. For example, the one-dimensional conductive fillers may include a conductive material based on silver nanowire.

In some example embodiments, the amount of the one-dimensional conductive fillers included in the mixed conductive fillers may be greater than the amount of the two-dimensional conductive fillers included in the mixed conductive fillers.

The biomimetic highly stretchable conductive dry adhesive patch according to example embodiments may be used or utilized as a skin patch and/or an adhesive patch using physical adhesive properties based on the mushroom-shaped micropillars (e.g., based on the tip portion having a width larger than the body portion) formed by replicating the cilia structures of the gecko lizard. In addition, the biomimetic highly stretchable conductive dry adhesive patch according to example embodiments may be used as a wearable electrode for sensing a biosignal (e.g., an electrocardiogram (ECG)) using electrical properties based on the mixed conductive fillers dispersed in the mushroom-shaped micropillars. The Adhesion, durability, etc. may be determined by an aspect ratio (AR) representing a ratio of a height to a width of each mushroom-shaped micropillar, and the electrical conductivity may be determined by the content of the mixed conductive fillers in the conductive polymer composite, a ratio of the one-dimensional conductive fillers and the two-dimensional conductive fillers, etc.

Hereinafter, the biomimetic highly stretchable conductive dry adhesive patch according to example embodiments will be described in detail with reference to specific experimental examples.

Experimental Examples and Applications to Wearable Devices

To manufacture or fabricate a mold, a SOI substrate including a handling layer, a buried oxide (BOX) insulation layer and a silicon layer that are sequentially stacked was used. Three SOI substrates including the silicon layers having thicknesses of about 10, 15 and 20 μm were prepared. A photoresist layer was formed on the silicon layer using a negative type photoresist SU-8 (trade name, MicroChem) and through a spin coating process. An exposure process was performed using a pre-patterned chrome mask including a hole array pattern with holes about 5 μm in diameter arranged in a square formation, and a development process was performed to remove the uncured photoresist. Thereafter, a DRIE was performed on the silicon layer until the BOX insulation layer was exposed, the silicon layer was additionally etched under the same conditions, and the photoresist pattern was removed. Based on a footing effect, mushroom-shaped holes were formed in which a diameter of a lower first part was about 7 μm and a diameter of a upper second part was about 5 μm, and thus the mold including the mushroom-shaped holes was obtained.

To prepare a conductive polymer composite or a conductive elastomer, PDMS base Sylgard 184 (trade name, Dow Corning) and carbon nanofillers were used. For the carbon nanofillers, carbon nanotube M95 (trade name, Carbon Nanomaterial Tech) was used as main fillers and one-dimensional conductive fillers, and carbon black, nanostructured graphite and graphene nanopowder were used as aid (or auxiliary) fillers and two-dimensional conductive fillers. The PDMS base and the carbon nanofillers were mixed at about 2,000 rpm for about 5 minutes, and a gas was removed or degassed at about 2,200 rpm for about 1 minute. Thereafter, PDMS curing agent was added and mixed at about 2,000 rpm for about 5 minutes, a gas was degassed at about 2,200 rpm for about 1 second, and thus the conductive polymer composite was obtained.

Before applying or spreading the conductive polymer composite on the mold including the mushroom-shaped holes, a surface treatment was performed on the mold. To use a SAM method, a fluorine based solution (tridecafluoro-1,1,2,2-tetrahydrooctyl)trichlorosilane and the mold were placed in a vacuum chamber, the solution was coated on a surface of the mold in a vapor atmosphere or environment. The interfacial energy of the mold was reduced by the surface treatment described above, and it was checked that the interfacial energy of the mold was reduced by measuring a contact angle of water droplets on the surface-treated mold.

To manufacture a conductive dry adhesive structure, the conductive polymer composite was poured onto the mold including the mushroom-shaped holes, and a thin elastic substrate was formed at the bottom of the conductive dry adhesive structure through a spin coating process at about 1,000 rpm for about 60 seconds. Thereafter, the conductive polymer composite and the mold were placed in a vacuum chamber for about 1 hour to remove a gas, the conductive polymer composite was cured at about 120° C. for about 2 hours, the cured conductive dry adhesive structure was carefully remove from the mold, and thus the conductive dry adhesive structure including mushroom-shaped micropillars for implementing the biomimetic highly stretchable conductive dry adhesive patch according to example embodiments was obtained. The mold was removed without damaging the micropillars by the surface treatment described above.

Figure 5:
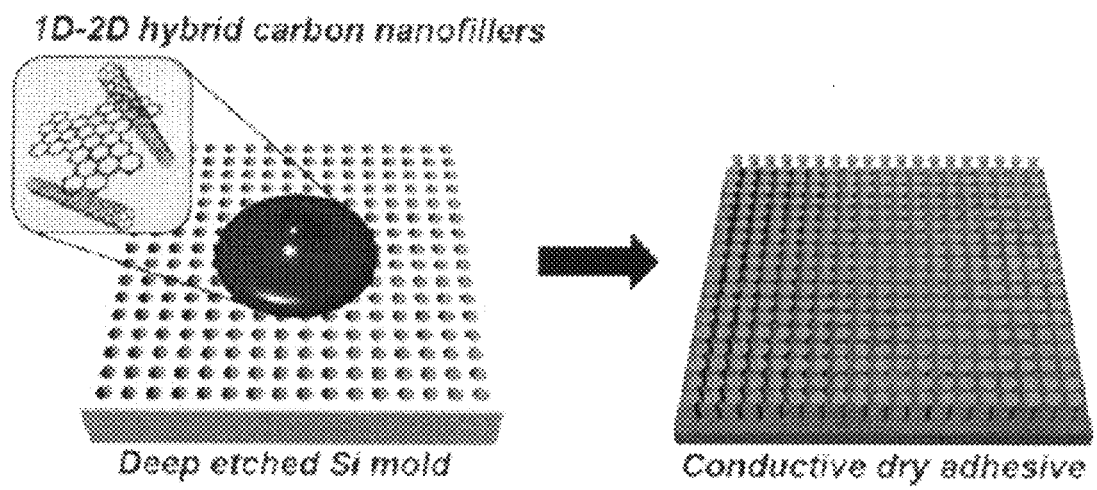
FIGS. 5 and 6 are diagrams illustrating a mold and a biomimetic highly stretchable conductive dry adhesive patch obtained by the method of FIG. 1.
Figure 6:
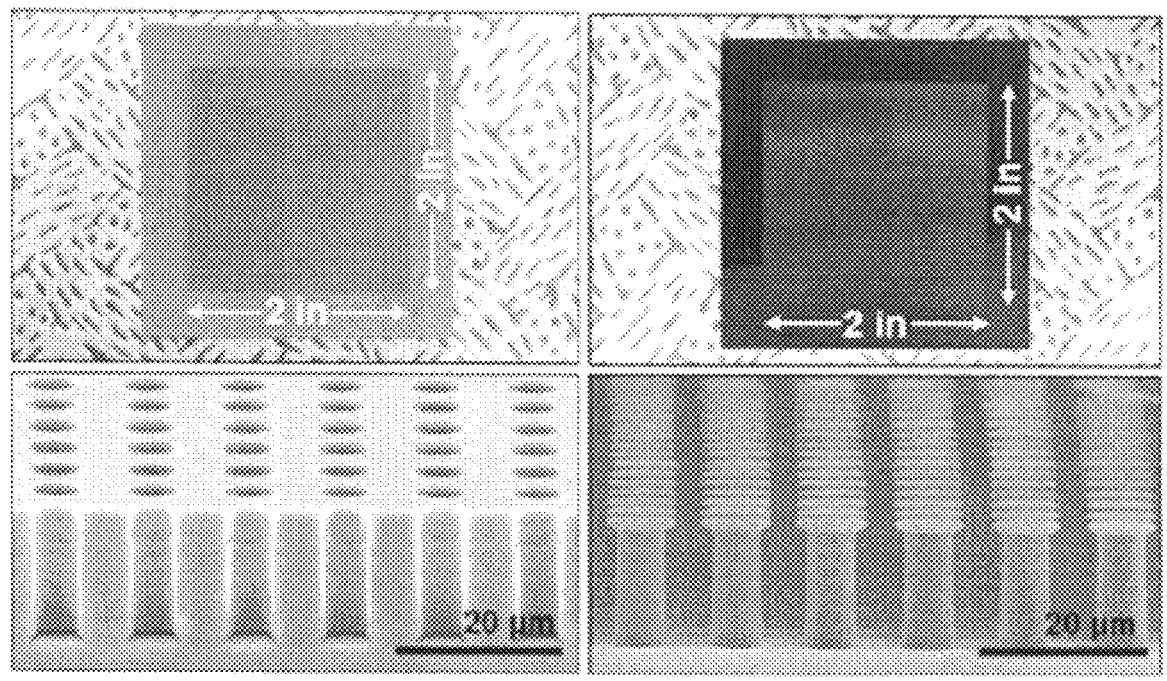

FIGS. 5 and 6 are diagrams illustrating a mold and a biomimetic highly stretchable conductive dry adhesive patch obtained by the method of FIG. 1.

Referring to FIG. 5, it may be seen that a biomimetic highly stretchable conductive dry adhesive patch (e.g., Conductive dry adhesive in FIG. 5) is obtained by vacuum-assisted capillary filling a viscous PDMS prepolymer in which 1D-2D hybrid carbon nanofillers are embedded with low loading rate on a mold (e.g., Deep etched Si mold in FIG. 5).

Referring to FIG. 6, it may be seen from upper images that a mold having a relatively large area of about 4 inch$^2$ and a biomimetic highly stretchable conductive dry adhesive patch formed by replicating a reverse structure of the mold are obtained. In addition, it may be seen from lower scanning electron microscope (SEM) images that mushroom-shaped holes and mushroom-shaped micropillars are uniformly formed and arranged.

As illustrated in FIGS. 4, 5 and 6, example embodiments will be described based on a case where each micropillar has a cylindrical shape, the inventive concepts are not limited thereto. For example, each micropillar may have any pillar or columnar shape with any shape (e.g., circular, elliptical, polygonal, etc.) in a plan view.

Figure 7:
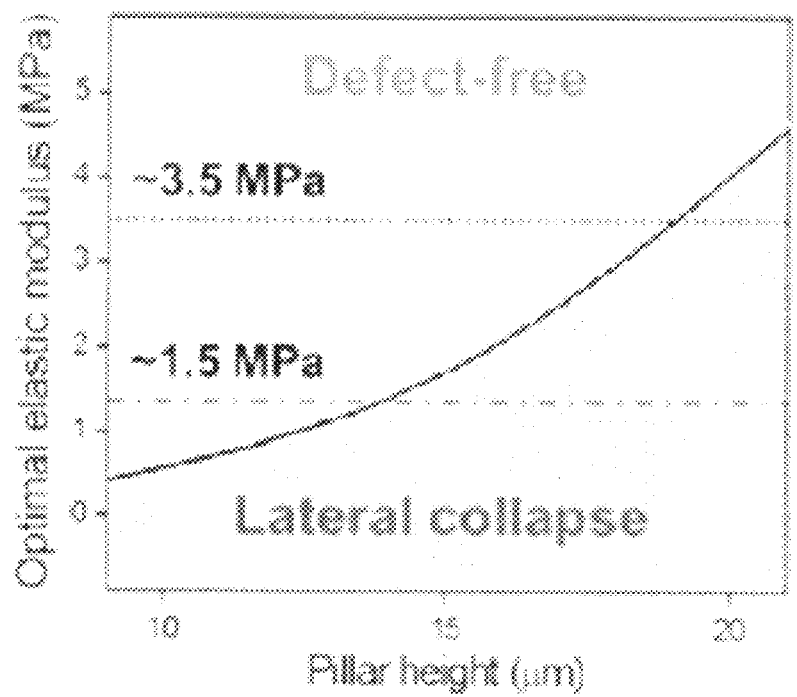
FIGS. 7, 8 and 9 are diagrams for describing the structural integrity according to an aspect ratio of a micropillar included in a biomimetic highly stretchable conductive dry adhesive patch according to example embodiments.
Figure 8:
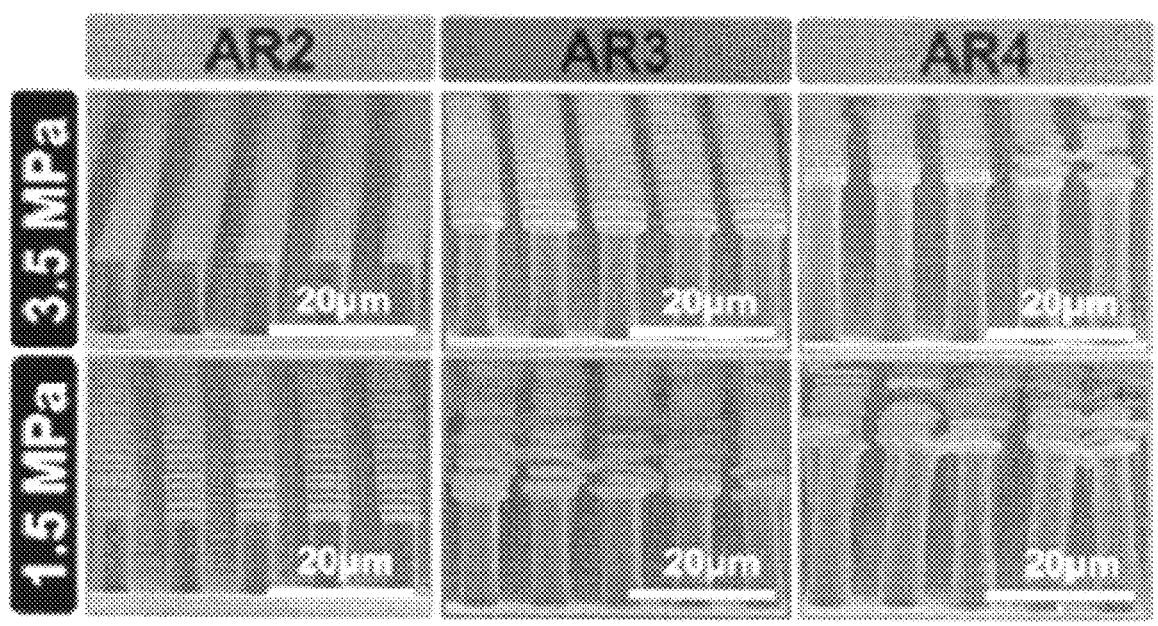
Figure 9:
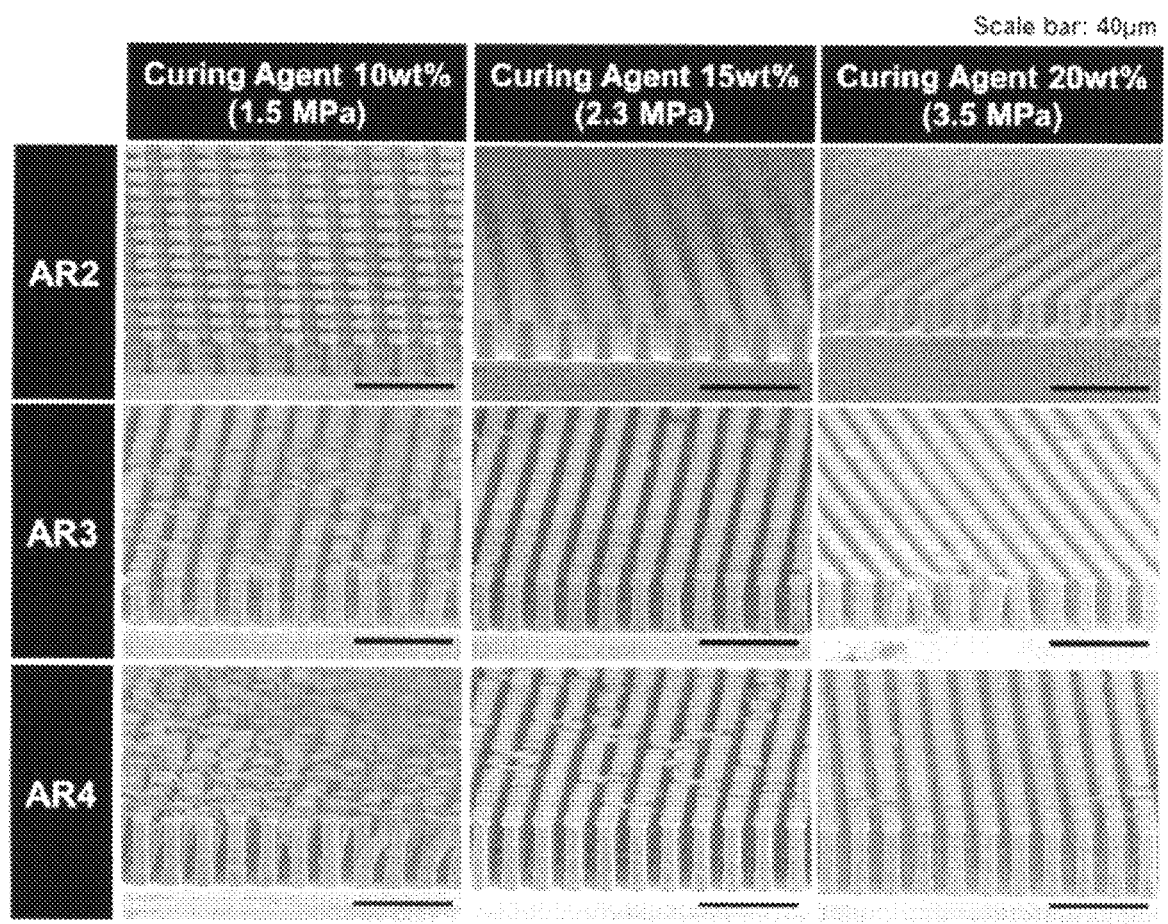

FIGS. 7, 8 and 9 are diagrams for describing the structural integrity according to an aspect ratio of a micropillar included in a biomimetic highly stretchable conductive dry adhesive patch according to example embodiments.

Referring to FIG. 7, an aspect ratio of a mushroom-shaped micropillar may be a ratio of a height (e.g., a total height including the thickness of the body portion and the thickness of the tip portion) of the micropillar to a width (e.g., the diameter of the body portion) of the micropillar, and may be obtained by dividing the height of the micropillar by the width of the micropillar. The adhesion area and the adhesion (or adhesion force) of the mimetic highly stretchable conductive dry adhesive patch may increase as the aspect ratio of the mushroom-shaped micropillar increases. However, since the micropillar is made of a soft (or elastic) material (e.g., the conductive polymer composite including PDMS), an achievable aspect ratio of the micropillar may be limited by the intrinsic elastic modulus of constructing the elastic material. A theoretical maximum height $h_{max}$ of the micropillar for preventing collapse (e.g., lateral collapse) of the micropillar may be expressed by Equation 1.

$$h_{max} = \left(\frac{\pi^4 E_{eff} R}{2^{11} \gamma_s (1-v^2)}\right)^{1/12} \left(\frac{12 E_{eff} R^3 (W/2)^2}{\gamma_s}\right)^{1/4} \quad \text{[Equation 1]}$$

In Equation 1, $E_{eff}$ represents an effective elastic modulus of the elastic material, R represents a radius of the body portion of the micropillar, W represents a period (or distance, space) between neighboring or adjacent micropillars, and $\gamma_s$ and v represent surface energy of the elastic material and Poisson's ratio of the elastic material, respectively.

From Equation 1, the required elastic modulus of the elastic material for defect-free replication of the micropillar may be obtained or extracted. For example, when the diameter of the body portion of the micropillar is about 5 μm, a graph showing an optimal elastic modulus (or elasticity) of the elastic material according to the height of the micropillar may be obtained as illustrated in FIG. 7. When it corresponds to a hatched area in a lower portion of the graph, the micropillar may collapse. When it corresponds to an area in an upper portion of the graph, the micropillar may be formed with defect-free (or without defects).

Referring to FIG. 8, the biomimetic highly stretchable conductive dry adhesive patches were manufactured in cases where the elastic modulus of the conductive polymer composite including PDMS and the mixed conductive fillers is about 1.5 MPa and about 3.5 MPa, and in cases where the aspect ratio of the micropillar is about 2, about 3 and about 4. In FIG. 8, AR2, AR3 and AR4 represent cases where the aspect ratio of the micropillar is about 2, 3 and 4, respectively. To implement the aspect ratio described above, the diameter of the body portion of the micropillar was fixed at about 5 μm, and the height of the micropillar was changed to about 10, 15 and 20 μm.

As illustrated by SEM images in FIG. 8, when the aspect ratio of the micropillar is about 2, no collapse occurred in both the micropillar including a relatively soft (or softer) conductive polymer composite having the elastic modulus of about 1.5 MPa and the micropillar including a relatively hard (or harder) conductive polymer composite having the elastic modulus of about 3.5 MPa. When the aspect ratio of the micropillar is about 3, collapse occurred in the micropillar including the conductive polymer composite having the elastic modulus of about 1.5 MPa, and no collapse occurred in the micropillar including the conductive polymer composite having the elastic modulus of about 3.5 MPa. When the aspect ratio of the micropillar is about 4, collapse occurred in both the micropillar including the conductive polymer composite having the elastic modulus of about 1.5 MPa and the micropillar including the conductive polymer composite having the elastic modulus of about 3.5 MPa. In other words, it may be confirmed that the calculation result described with reference to FIG. 7 is valid.

Referring to FIG. 9, the biomimetic highly stretchable conductive dry adhesive patches were manufactured in cases where a curing degree of the conductive polymer composite is adjusted differently, and in the cases where the aspect ratio of the micropillar is about 2, 3 and 4. The elastic modulus of the conductive polymer composite may increases as the content of the curing agent increases, and thus the conductive polymer composite may become hard. As illustrated by SEM images in FIG. 9, it may be seen that collapse of the micropillars per a unit area is reduced as the elastic modulus of the conductive polymer composite increases (e.g., as the conductive polymer composite becomes hard).

Figure 10:
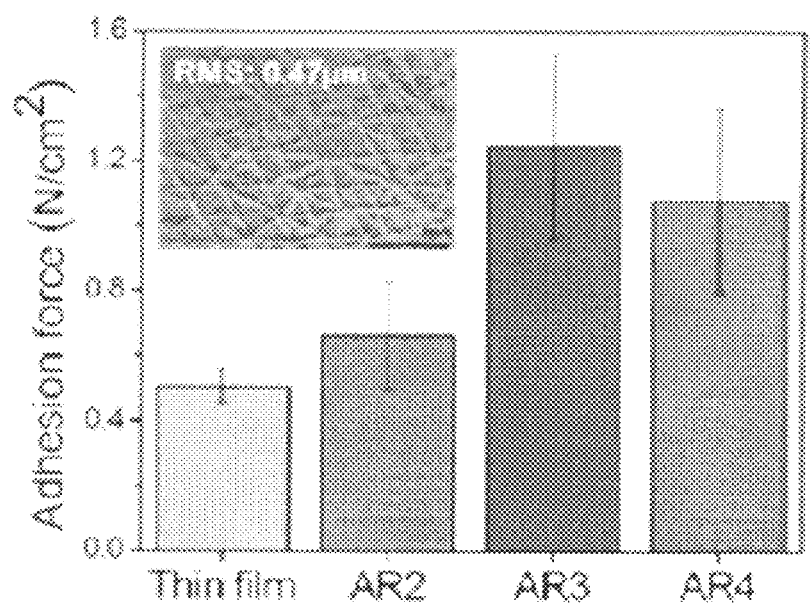
FIGS. 10, 11 and 12 are diagrams for describing the adhesion according to an aspect ratio of a micropillar included in a biomimetic highly stretchable conductive dry adhesive patch according to example embodiments.
Figure 11:
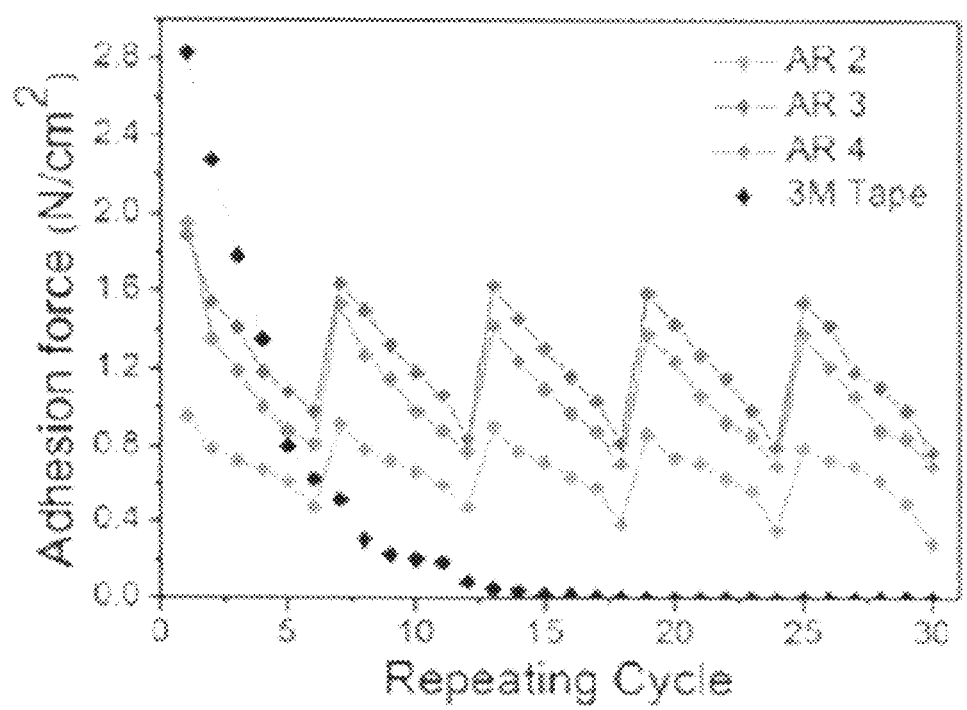
Figure 12:
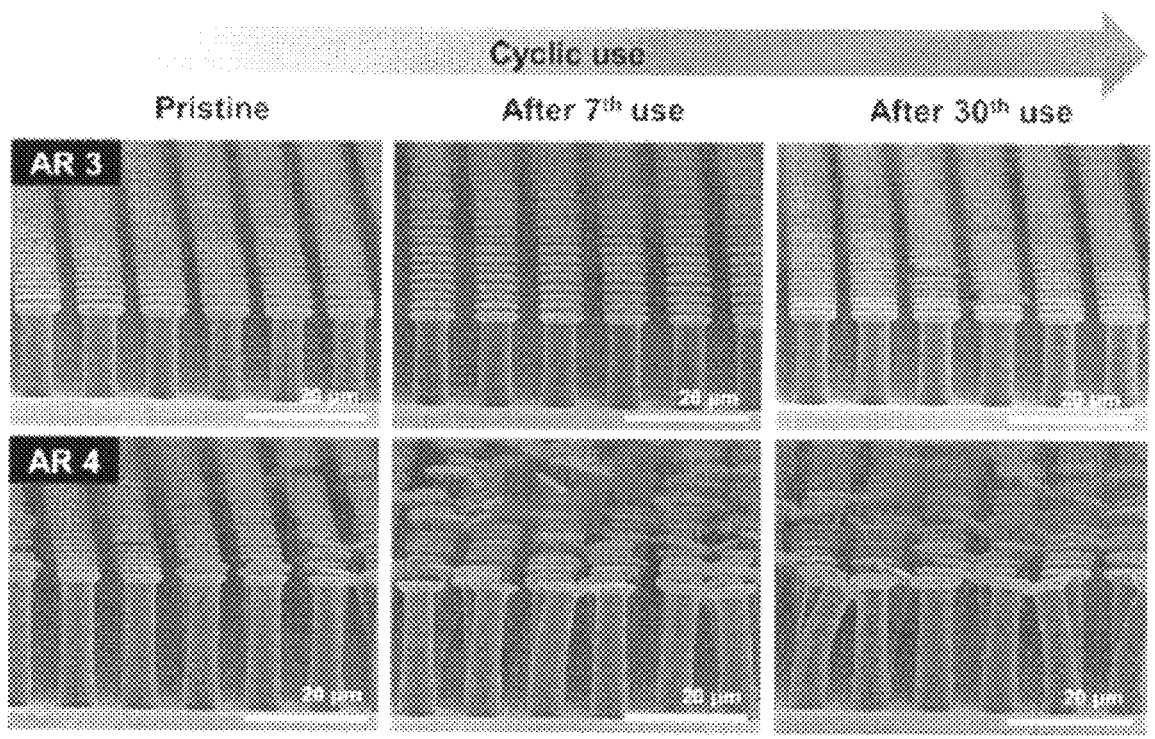

FIGS. 10, 11 and 12 are diagrams for describing the adhesion according to an aspect ratio of a micropillar included in a biomimetic highly stretchable conductive dry adhesive patch according to example embodiments.

Referring to FIG. 10, an average adhesion of the biomimetic highly stretchable conductive dry adhesive patch was measured in the cases where the aspect ratio of the mushroom-shaped micropillar is about 2, 3 and 4. A skin surface having a root-mean-square (RMS) value of about 0.47 μm was used as a target surface, and the biomimetic highly stretchable conductive dry adhesive patches were manufactured using a conductive polymer composite with an elastic modulus of about 2.3 MPa.

As illustrated in FIG. 10, it may be seen that the biomimetic highly stretchable conductive dry adhesive patch according to example embodiments has excellent adhesion force as compared with a thin film that does not include the micropillar, and the adhesion force is particularly excellent in the case where the aspect ratio is about 3 (AR3) among the cases where the aspect ratio is about 2, 3 and 4 (AR2, AR3 and AR4).

Referring to FIG. 11, a change in adhesion force was measured according to repeatedly attachment and detachment of the biomimetic highly stretchable conductive dry adhesive patch in the cases where the aspect ratio of the micropillar is about 2, 3 and 4. Conditions of the target surface and manufacturing the biomimetic highly stretchable conductive dry adhesive patch were substantially the same as described with reference to FIG. 10. In addition, the biomimetic highly stretchable conductive dry adhesive patch was washed with water after repeating attachment and detachment six times.

As illustrated in FIG. 11, it may be seen that the biomimetic highly stretchable conductive dry adhesive patch according to example embodiments has low initial adhesion but does not cause degradation or deterioration of adhesion even after repeated use as compared with a commercially available wet adhesive tape (3M Tape, trade name), and the adhesion force is particularly excellent in the case where the aspect ratio is about 3 or 4 (AR3 or AR4) among the cases where the aspect ratio is about 2, 3 and 4 (AR2, AR3 and AR4). In addition, as will be described with reference to FIGS. 19A, 19B and 19C, the biomimetic highly stretchable conductive dry adhesive patch may have super (or very strong) hydrophobicity, and thus it may be seen that the adhesion is restored after washing with water.

Referring to FIG. 12, a change of the micropillar was observed according to repeatedly attachment and detachment of the biomimetic highly stretchable conductive dry adhesive patch in the cases where the aspect ratio of the micropillar is about 3 and 4.

As illustrated by SEM images in FIG. 12, it may be seen that there is almost no collapse of the micropillar in the case where the aspect ratio is about 3 (AR3) even after repeating attachment and detachment about 30 times, however, the micropillar is relatively collapsed in the case where the aspect ratio is about 4 (AR4) repeating attachment and detachment about 30 times, as compared with a pristine of the biomimetic highly stretchable conductive dry adhesive patch.

Based on the features described with reference to FIGS. 7, 8, 9, 10, 11 and 12, the mushroom-shaped micropillar included in the biomimetic highly stretchable conductive dry adhesive patch according to example embodiments may have a high-aspect-ratio. For example, the aspect ratio of the micropillars may have a high-aspect-ratio within a range of about 2 to about 4, preferably within a range of about 2.5 to about 3.5, and more preferably about 3. If the aspect ratio of the micropillar is less than about 2, the average adhesion of the biomimetic highly stretchable conductive dry adhesive patch may be reduced. If the aspect ratio of the micropillar is greater than about 4, the adhesion durability of the biomimetic highly stretchable conductive dry adhesive patch may be degraded as the micropillar is collapsed.

FIGS. 13A, 13B, 14, 15A, 15B, 16A and 16B are diagrams for describing the electrical conductivity and flexibility/elasticity according to a type of mixed conductive fillers included in a biomimetic highly stretchable conductive dry adhesive patch according to example embodiments.

Figure 13A:
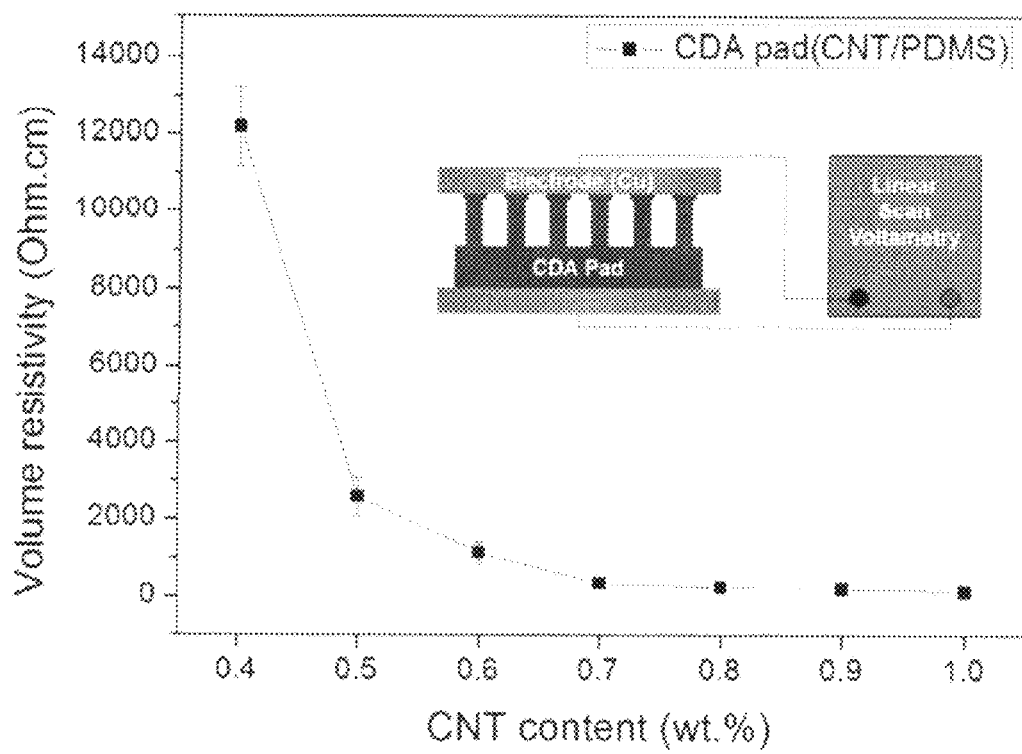

Referring to FIG. 13A, a volume resistivity of the biomimetic highly stretchable conductive dry adhesive patch was measured by using only carbon nanotubes, which are one-dimensional conductive materials, as conductive fillers, and by differently adjusting the content of carbon nanotubes included in PDMS.

As illustrated in FIG. 13A, it may be seen that the volume resistivity decreases when the content of the carbon nanotubes is about 1.0 weight percent (wt %) than when the content of the carbon nanotubes is about 0.4 weight percent, based on a total weight of the PDMS and the carbon nanotubes (e.g., based on a total weight of the conductive polymer composite). The biomimetic highly stretchable conductive dry adhesive patch may require lower volume resistivity to be used as a wearable electrode for sensing biological signals, however, the volume resistivity may not decrease anymore even if the content of the carbon nanotubes exceeds about 1.0 weight percent based on the total weight of the conductive polymer composite. In addition, if the content of the carbon nanotubes exceeds about 1.0 weight percent based on the total weight of the conductive polymer composite, a problem may occur in that the viscosity of the conductive polymer composite, which is a liquid elastomer including the PDMS and the carbon nanotubes, increases.

In some example embodiments, in FIG. 13A and embodiments to be described later, the carbon nanotubes may include multiwalled CNTs (MWCNTs). However, the carbon nanotubes are not limited thereto. For example, the carbon nanotubes may include singlewalled carbon nanotubes (SWCNTs).

Figure 13B:
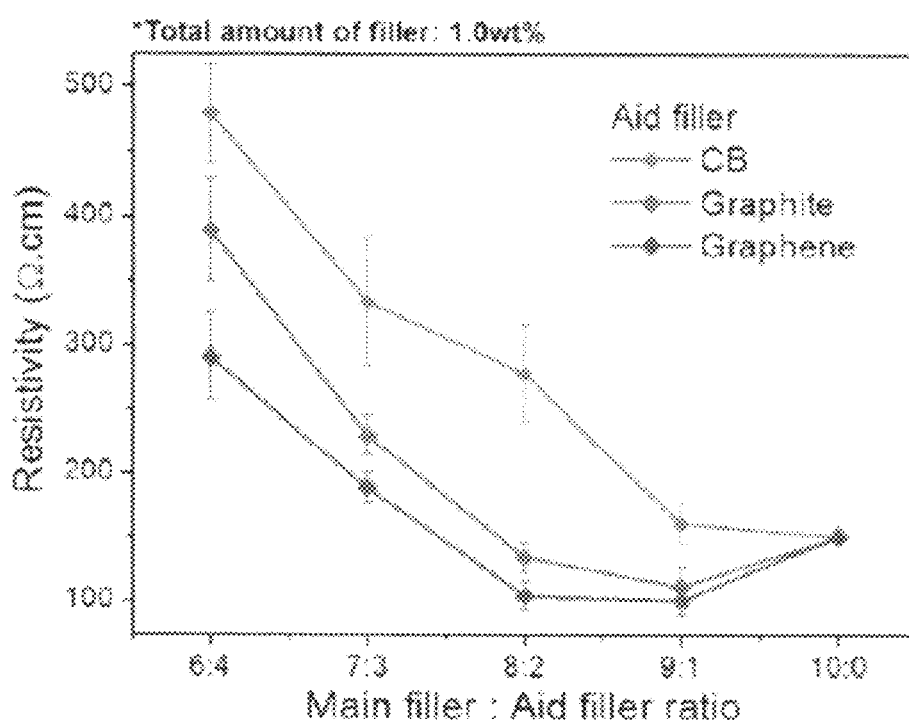

Referring to FIG. 13B, a resistivity of the biomimetic highly stretchable conductive dry adhesive patch was measured by using the carbon nanotubes as the main conductive fillers, by using carbon black (CB), nanostructured graphite and graphene nanopowder, which are two-dimensional conductive materials, as the aid conductive fillers, and by differently adjusting a ratio of the main conductive fillers and the aid conductive fillers. For all cases, the content of the mixed conductive fillers was maintained to about 1.0 weight percent based on a total weight of the PDMS and the mixed conductive fillers (e.g., based on a total weight of the conductive polymer composite).

As illustrated in FIG. 13B, it may be seen that the resistivity decreases in the cases where the nanostructured graphite and the graphene nanopowder are used as the aid conductive fillers as compared with a case where only the carbon nanotubes are used as the conductive filler (e.g., a case where a ratio of the main conductive fillers and the aid conductive fillers is about 10:0). For example, the resistivity may decrease when a ratio of the main conductive fillers and the aid conductive fillers is within a range of about 8:2 to about 9.99:0.01, and thus the electrical conductivity may be improved. However, the carbon black may have a smaller particle size than the nanostructured graphite and the graphene nanopowder, and thus the degree of improvement in the electrical conductivity may be relatively small.

Referring to FIG. 14, it may be seen that performance of the flexibility and/or elasticity of the PDMS including only the carbon nanotubes alone or together with the carbon nanotubes and the aid conductive fillers in a ratio of about 9:1 may be slightly reduced as compared with a bare PDMS which does not include any conductive filler. However, the flexibility and/or elasticity of the PDMS including the conductive fillers illustrated in FIG. 14 may be sufficient to implement the biomimetic highly stretchable conductive dry adhesive patch according to example embodiments. Particularly, since there is almost no difference in the performance of the flexibility and/or elasticity of the PDMS including the carbon nanotubes and the aid conductive fillers as compared with the PDMS including only the carbon nanotubes alone, it may be more preferable or desirable to ensure higher electrical conductivity by using the aid conductive fillers together.

Figure 15A:
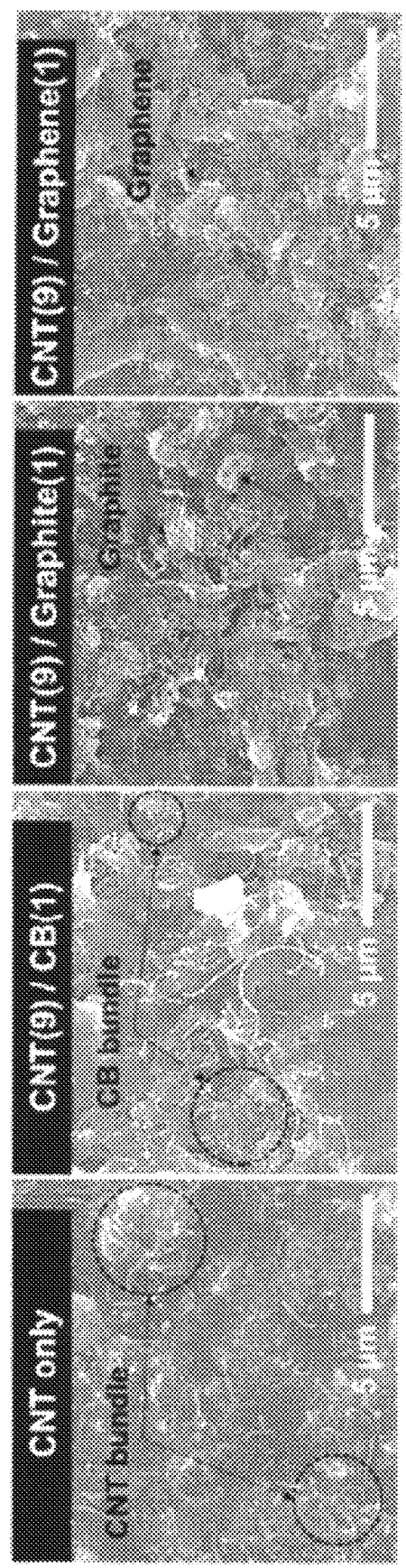
Figure 15B:
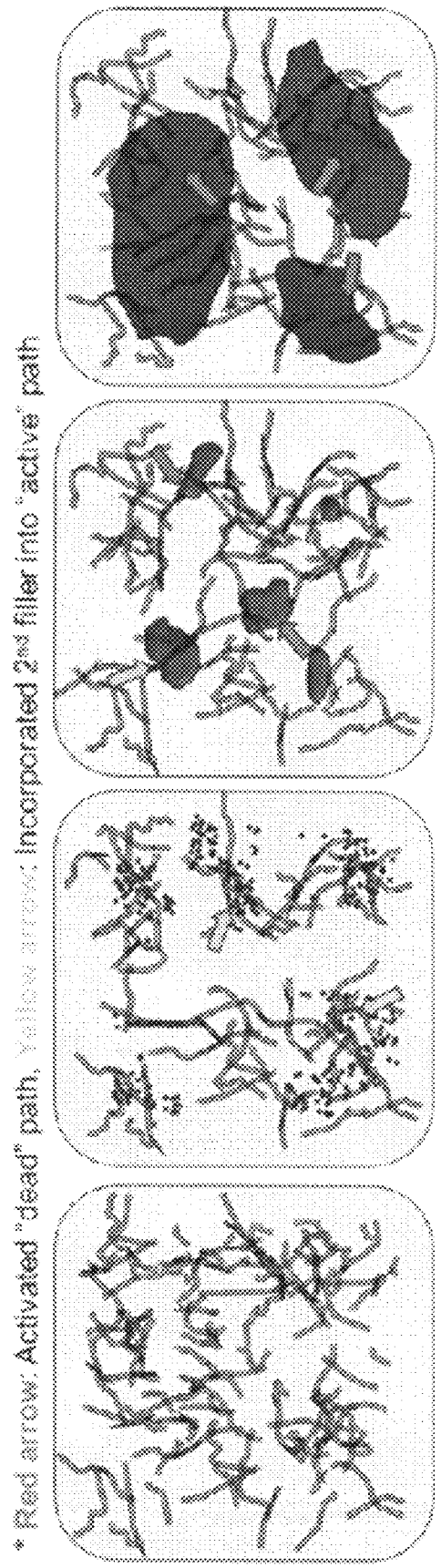

Referring to FIGS. 15A and 15B, SEM images of the PDMS including only the carbon nanotubes and the PDMS including the carbon nanotubes and the aid conductive fillers in a ratio of about 9:1 are illustrated in FIG. 15A, and a degree of dispersion of the conductive fillers in corresponding PDMS is conceptually illustrated in FIG. 15B.

As illustrated in FIG. 15B, when only the carbon nanotubes are included in the PDMS (e.g., CNT only), a density of an one-dimensional conductive network may be relatively low, and thus an electrical conductivity may be relatively low. When the carbon nanotubes and the aid conductive fillers are included in the PDMS, the two-dimensional plate-like conductive materials may be connected to weak connections of the one-dimensional conductive network, and thus a density and an electrical conductivity of the 1D-2D hybrid conductive network may increase. In addition, an electrical breakdown that occurs while stretching or bending the PDMS may be reduced by the 1D-2D hybrid conductive network.

For example, dead percolation regions where conductive paths are disconnected may be electrically connected to each other by a small amount of wide and flat two-dimensional aid conductive fillers, such as graphite and graphene. In other words, as the graphite and the graphene, which are two-dimensional conductive fillers, are disposed in an empty area where the carbon nanotubes, which are one-dimensional conductive fillers, are not dispersed, carbon nanotubes that were not electrically connected may be electrically connected by the two-dimensional conductive fillers, a dead percolation path may be turned into an activation path, and thus the aid conductive fillers may operate as an activator to revive the partially dead percolation region.

Figure 16A:
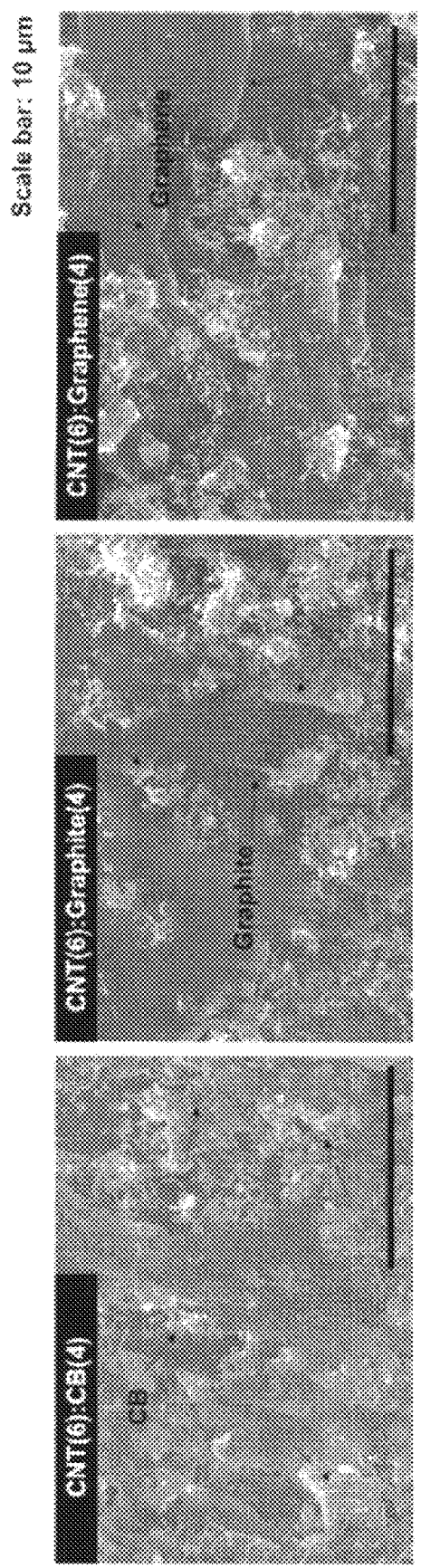
Figure 16B:
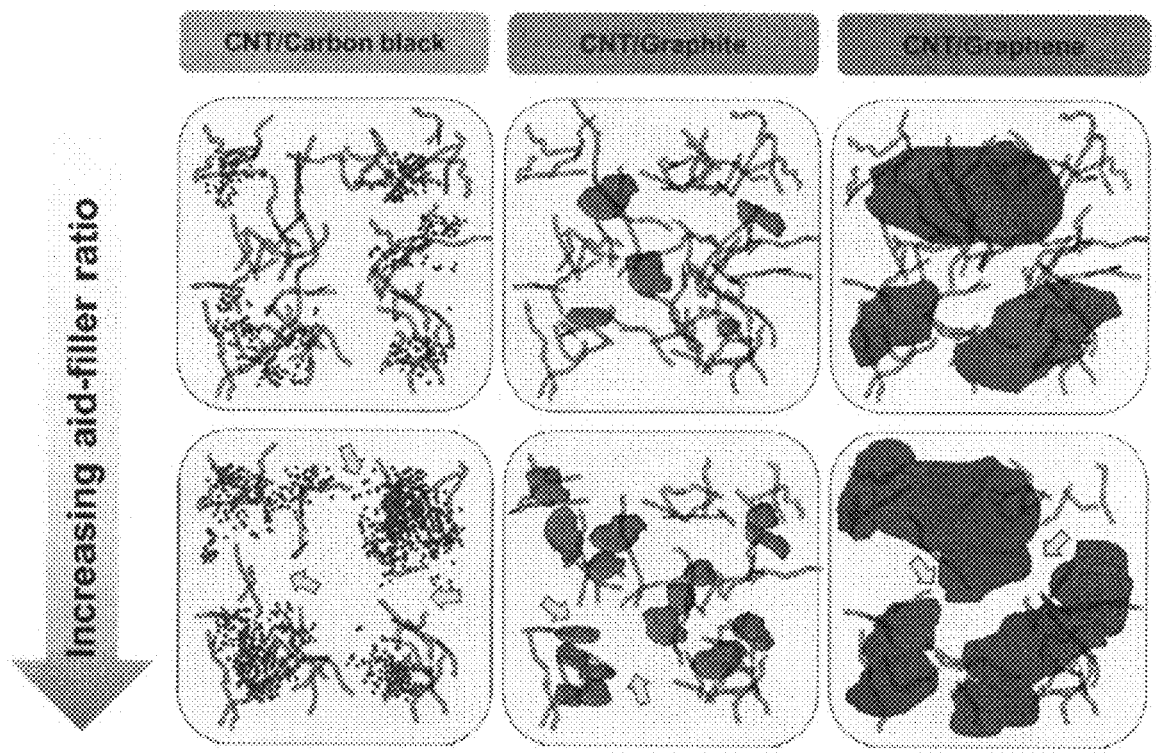

Referring to FIGS. 16A and 16B, SEM images of the PDMS including the carbon nanotubes and the aid conductive fillers in a ratio of about 6:4 are illustrated in FIG. 16A, and a degree of dispersion of the conductive fillers in corresponding PDMS with an increase of the aid conductive fillers is conceptually illustrated in FIG. 16B.

As illustrated in FIG. 16B, when a ratio of the two-dimensional conductive fillers which is the aid conductive fillers increases, an areal coverage of the two-dimensional conductive fillers may be excessively or exponentially increased compared to that of the carbon nanotubes which are the one-dimensional conductive fillers, and a major electrical path may be confused. Thus, an electrical synergetic effect between the one-dimensional conductive fillers and the two-dimensional conductive fillers may disappear, and the electrical conductivity may be rather deteriorated or degraded.

Based on the features described with reference to FIGS. 13A, 13B, 14, 15A, 15B, 16A and 16B, the amount of the mixed conductive fillers dispersed in the elastic structure of the biomimetic highly stretchable conductive dry adhesive patch according to example embodiments may be less than or equal to about 1.0 weight percent based on the total weight of the elastic structure and the mixed conductive fillers (e.g., the total weight of the conductive polymer composite including the liquid elastomer and the mixed conductive fillers), and preferably within a range of about 0.5 weight percent to about 1.0 weight percent. If the amount of the mixed conductive fillers is less than about 0.5 weight percent, it may be difficult to achieve a desired electrical conductivity. If the amount of the mixed conductive fillers is greater than about 1.0 weight percent, the viscosity of the conductive polymer composite may increase, and thus it may be difficult to manufacture the elastic structure using the capillary filling.

In addition, based on the features described with reference to FIGS. 13A, 13B, 14, 15A, 15B, 16A and 16B, the ratio of the one-dimensional conductive fillers and the two-dimensional conductive fillers in the mixed conductive fillers dispersed in the elastic structure of the biomimetic highly stretchable conductive dry adhesive patch according to example embodiments may be within a range of about 8:2 to about 9.99:0.01, preferably within a range of about 8.5:1.5 to about 9.5:0.5, and more preferably about 9:1. If the ratio of the two-dimensional conductive fillers is greater than about 20% or less than about 0.01%, it may be difficult to achieve a desired electrical conductivity.

Figure 17:
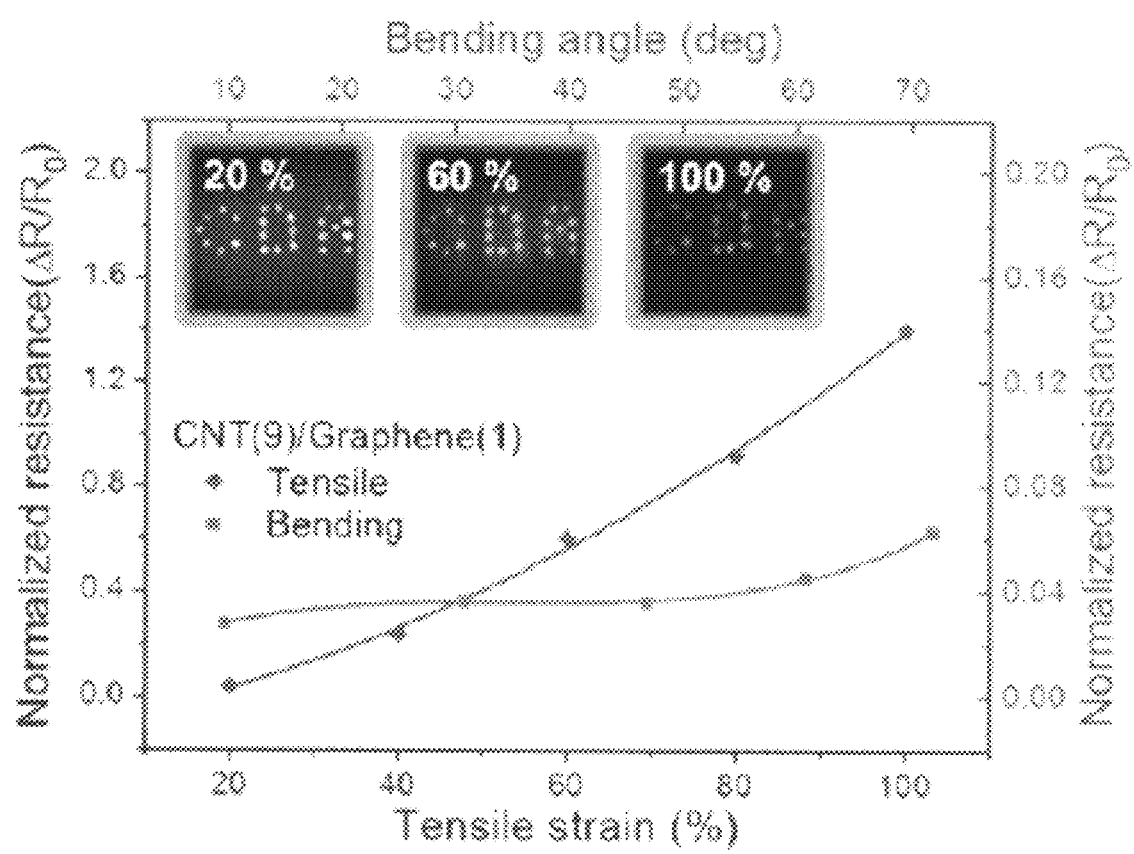
FIGS. 17 and 18 are diagrams for describing the electrical characteristic of a biomimetic highly stretchable conductive dry adhesive patch according to example embodiments.
Figure 18:
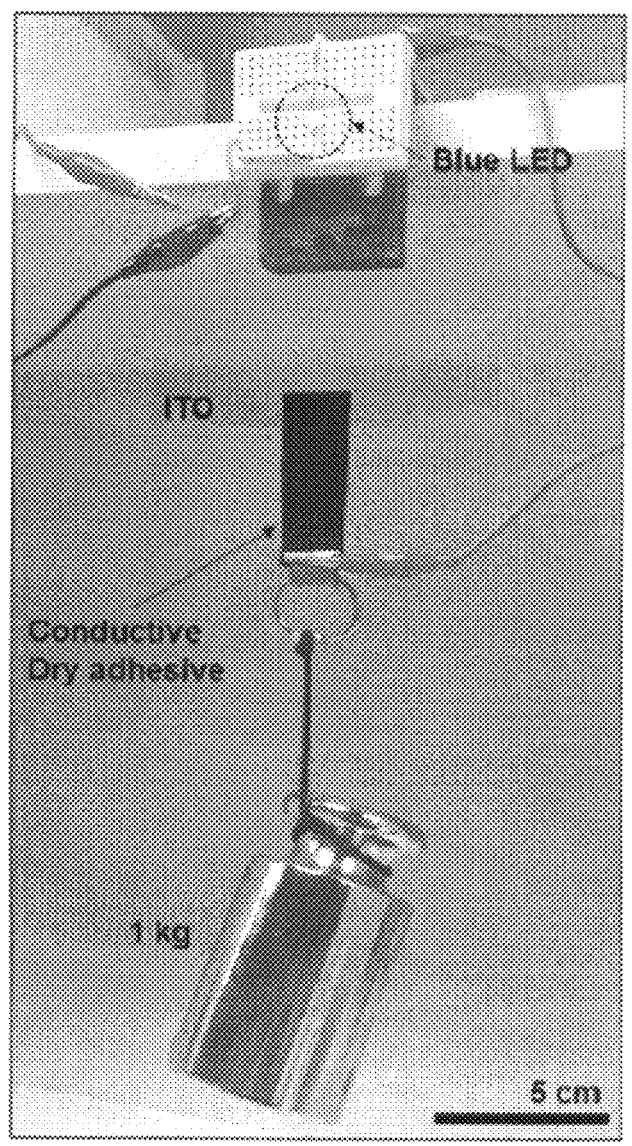

FIGS. 17 and 18 are diagrams for describing the electrical characteristic of a biomimetic highly stretchable conductive dry adhesive patch according to example embodiments.

Referring to FIG. 17, the biomimetic highly stretchable conductive dry adhesive patch according to example embodiments including the mixed conductive fillers of about 1.0 weight percent in which the ratio of the carbon nanotubes which are the one-dimensional conductive fillers and the graphenes which are the two-dimensional conductive fillers is about 9:1 was manufactured.

As described with reference to FIGS. 15A and 15B, the electrical breakdown that occurs while stretching or bending the biomimetic highly stretchable conductive dry adhesive patch may be reduced by the 1D-2D hybrid conductive network, and thus the biomimetic highly stretchable conductive dry adhesive patch may have excellent tensile and bending characteristics as illustrated in FIG. 17. For example, it may be seen that the biomimetic highly stretchable conductive dry adhesive patch has a relatively linearized change in a normalized resistance (e.g., a ratio of an initial resistance $R_0$ to a resistance $\Delta R$ after tensile deformation) even when elongated to about twice its initial state (e.g., even if a tensile strain becomes about 100%), and the normalized resistance of the biomimetic highly stretchable conductive dry adhesive patch is relatively unchanged and maintained even when it is bent to about 70 degrees.

Referring to FIG. 18, the biomimetic highly stretchable conductive dry adhesive patch according to example embodiments was attached to an indium tin oxide (ITO) film electrically connected to a light emitting diode (LED), a weight of about 1 kg was hung on the biomimetic highly stretchable conductive dry adhesive patch, and then the LED was successfully turned on. Thus, it may be seen that the biomimetic highly stretchable conductive dry adhesive patch simultaneously or concurrently plays a role of an electrode having electrical conductivity and an adhesive having adhesive property.

Figure 19A:
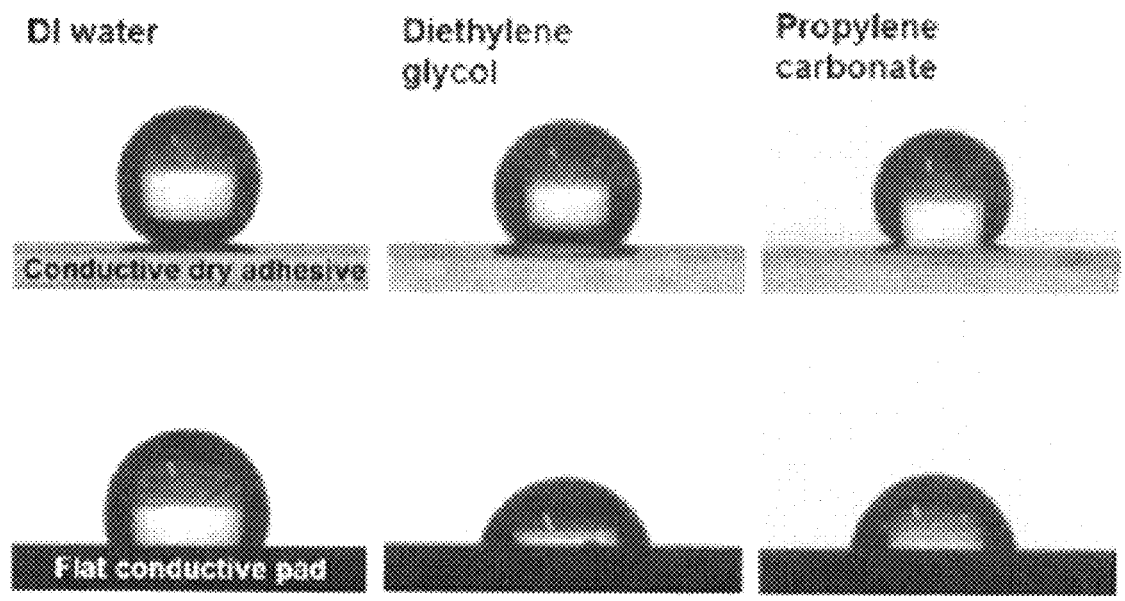
FIGS. 19A, 19B and 19C are diagrams for describing the hydrophobicity and durability/reusability of a biomimetic highly stretchable conductive dry adhesive patch according to example embodiments.
Figure 19B:
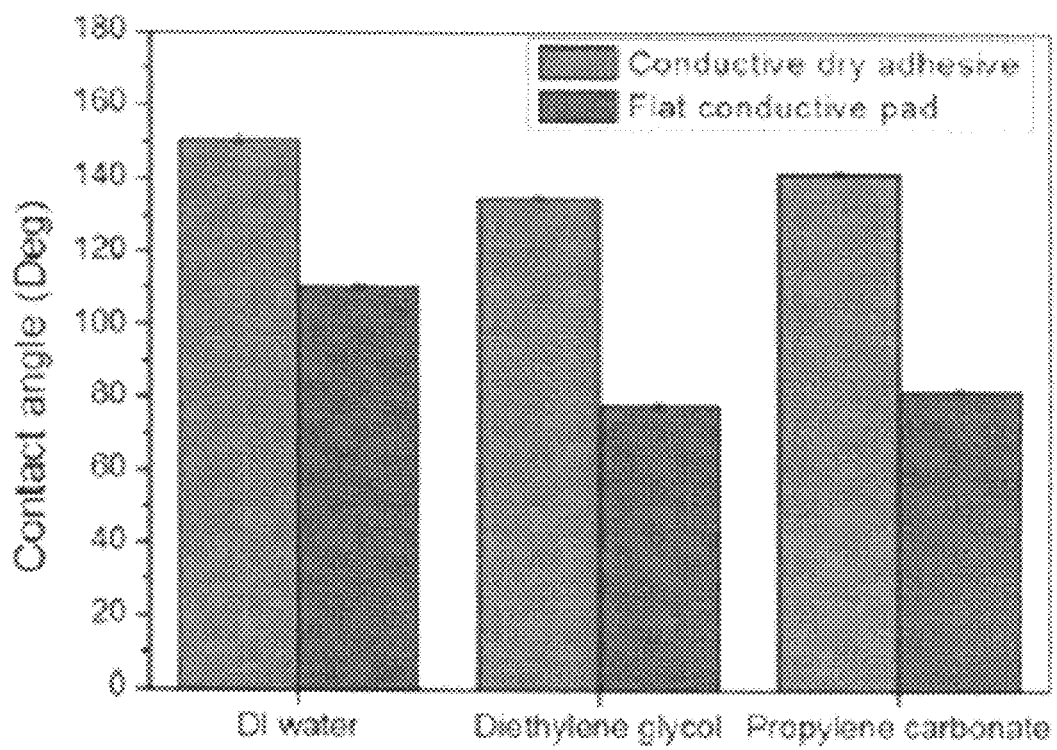
Figure 19C:
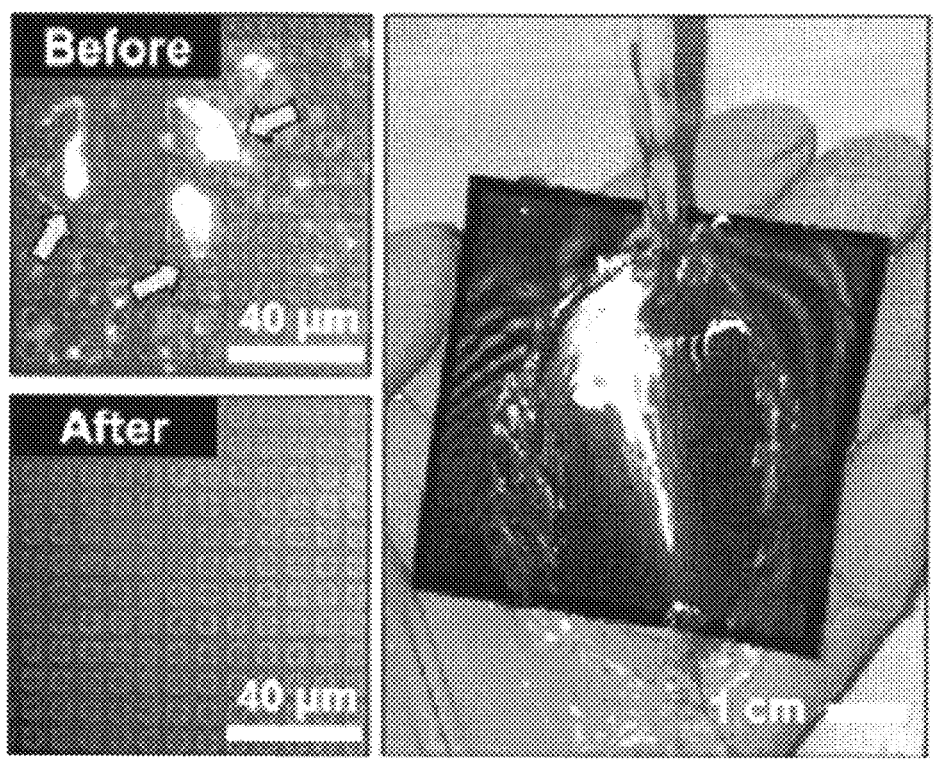

FIGS. 19A, 19B and 19C are diagrams for describing the hydrophobicity and durability/reusability of a biomimetic highly stretchable conductive dry adhesive patch according to example embodiments.

Referring to FIGS. 19A and 19B, deionized (DI) or pure water, diethylene glycol and propylene carbonate were dropped onto a surface of the biomimetic highly stretchable conductive dry adhesive patch (e.g., Conductive dry adhesive in FIGS. 19A and 19B) including the mushroom-shaped micropillars and a surface of a flat conductive pad, and contact angles were observed.

As illustrated in FIGS. 19A and 19B, it may be seen that the contact angles of the droplets on the biomimetic highly stretchable conductive dry adhesive patch including the mushroom-shaped micropillars are large as compared with the flat conductive pad, and the biomimetic highly stretchable conductive dry adhesive patch including the mushroom-shaped micropillars has the super hydrophobicity.

Referring to FIG. 19C, when the biomimetic highly stretchable conductive dry adhesive patch including the mushroom-shaped micropillars was washed with water, dusts attached to the surface of the biomimetic highly stretchable conductive dry adhesive patch were simply removed. In addition, the adhesion may be restored after washing with water as described with reference to FIG. 11. Thus, the biomimetic highly stretchable conductive dry adhesive patch may be used semi-permanently if there is no damage to the micropillars.

Figure 20:
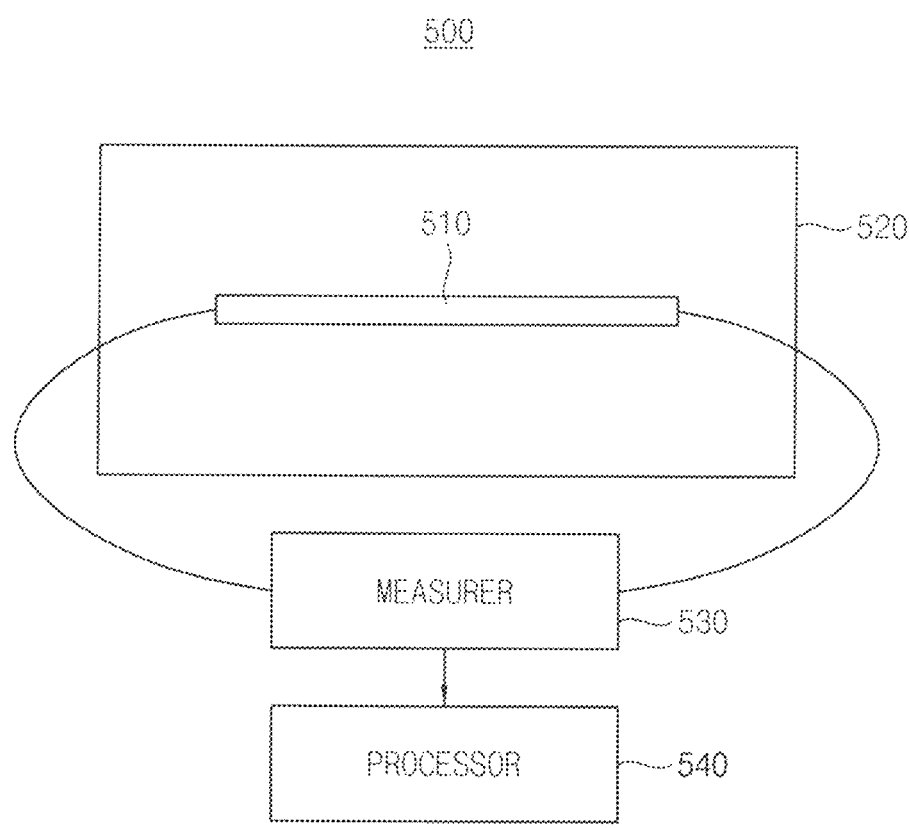
FIG. 20 is a block diagram illustrating a wearable device including a biomimetic highly stretchable conductive dry adhesive patch according to example embodiments.

FIG. 20 is a block diagram illustrating a wearable device including a biomimetic highly stretchable conductive dry adhesive patch according to example embodiments.

Referring to FIG. 20, a wearable device 500 includes a biomimetic highly stretchable conductive dry adhesive patch 510, a measurer 530 and a processor 540. The wearable device 500 may further include a frame 520.

The biomimetic highly stretchable conductive dry adhesive patch 510 includes a plurality of micropillars formed by replicating the numerous cilia structures that exist on the sole of the gecko lizard. The conductive network is formed in the biomimetic highly stretchable conductive dry adhesive patch 510 by dispersing the mixed conductive fillers in which the one-dimensional conductive fillers and the two-dimensional conductive fillers are mixed. Thus, biomimetic highly stretchable conductive dry adhesive patch 510 may have excellent adhesion properties and adhesion durability, as well as excellent flexibility, elasticity and electrical conductivity, and may be applied as a wearable electrode for detecting biosignals with high performance.

The measurer 530 is connected to the biomimetic highly stretchable conductive dry adhesive patch 510, and measures a signal (e.g., the biosignals) sensed by the biomimetic highly stretchable conductive dry adhesive patch 510. For example, the measurer 530 may be an electrocardiogram measurer. For another example, the measurer 530 may be a resistance measurer that measures a change in a resistance due to a tensile strain applied to the biomimetic highly stretchable conductive dry adhesive patch 510.

The processor 540 performs a predetermined data processing operation based on an output of the measurer 530.

The frame 520 may be formed of a flexible material, and may be attached to a human body or worn on the human body. In some example embodiments, the frame 520 may be omitted.

In some example embodiments, the wearable device 500 may include a smart watch, a wrist band electronic device, a wearable computer, a shoes-type electronic device, a clothes-type electronic device, or the like.

FIGS. 21A, 21B, 21C, 21D and 21E are diagrams illustrating examples of using a biomimetic highly stretchable conductive dry adhesive patch according to example embodiments as an electrocardiogram measurer.

Referring to FIGS. 21A and 21B, electrocardiograms were measured in dry conditions and underwater conditions using a commercially available electrocardiogram system (3M adhesive, trade name) and an electrocardiogram system including the biomimetic highly stretchable conductive dry adhesive patch according to example embodiments as an electrocardiogram measuring electrode.

As illustrated in FIGS. 21A and 21B, it may be seen that the biomimetic highly stretchable conductive dry adhesive patch according to example embodiments maintains a conformal contact with a skin of a human body not only in the drying condition but also in the underwater condition, and P, QRS and T curves which are clearly distinguished are observed in both the drying condition and the underwater condition. The P, QRS, and T curves may represent a number of parameters that are included in an electrocardiogram and are evaluated diagnostically, and may provide medical information associated with cardiovascular disease.

Figure 21C:
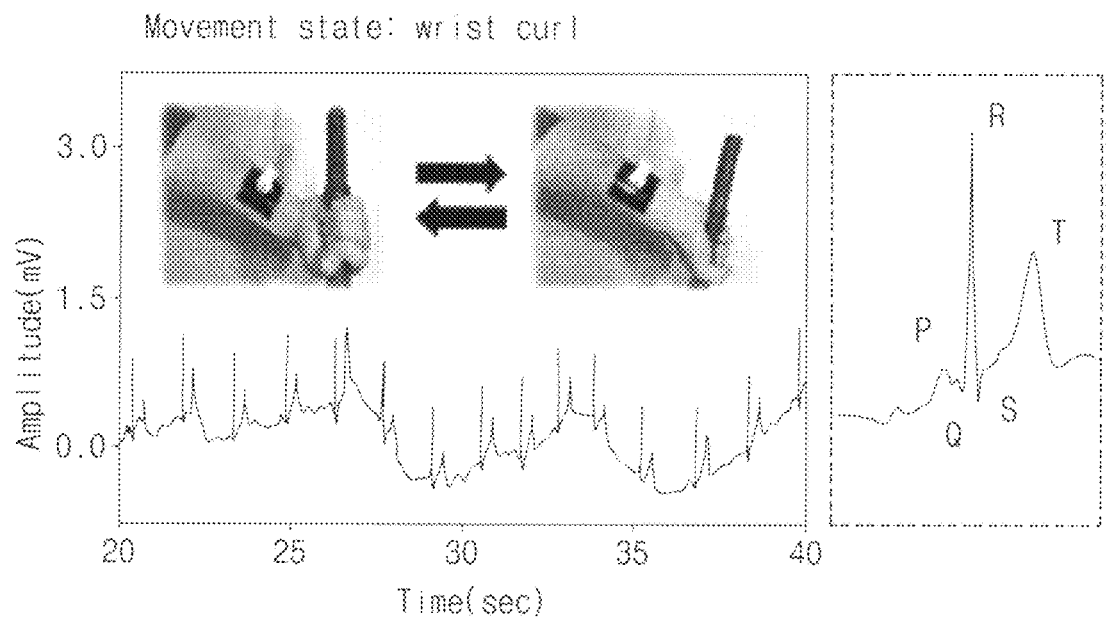
Figure 21D:
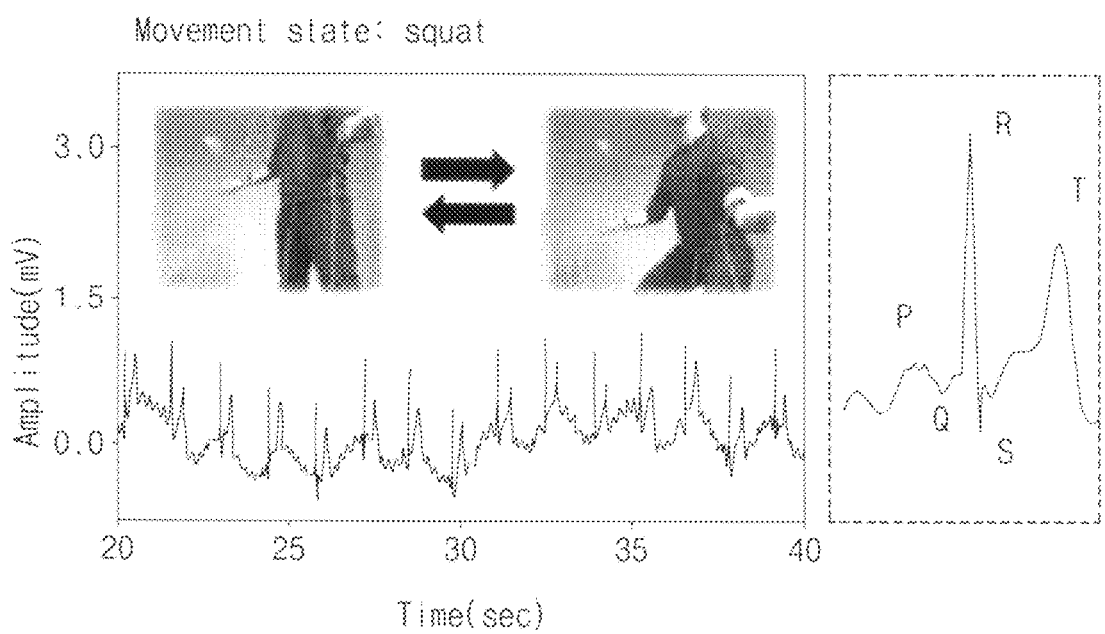
Figure 21E:
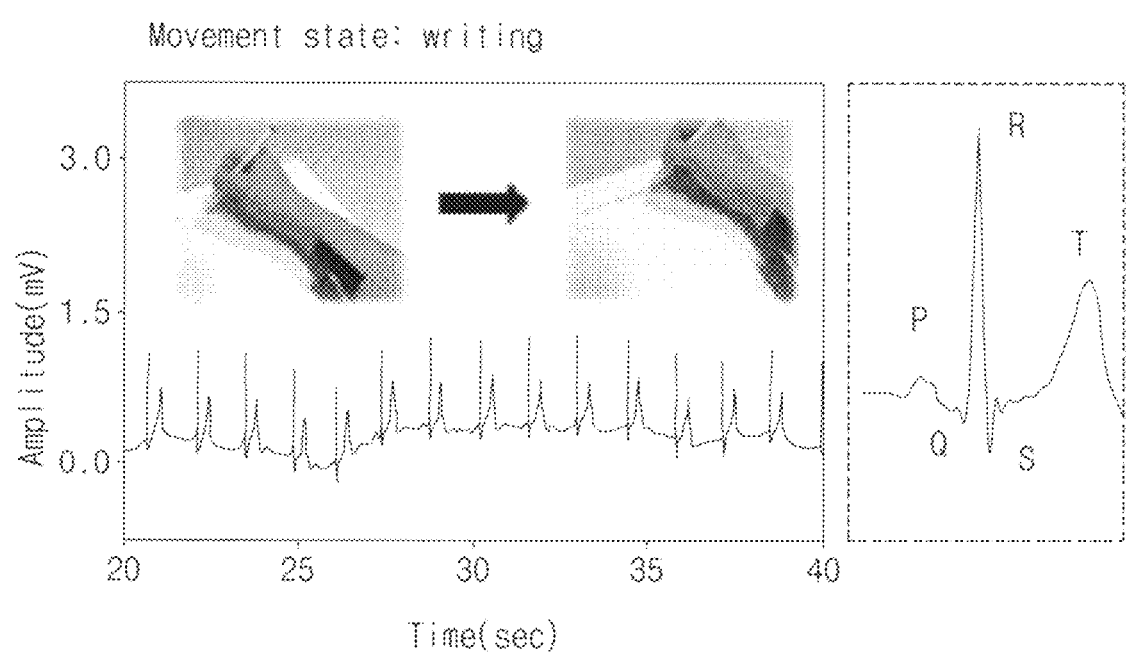

Referring to FIGS. 21C, 21D and 21E, it may be seen that the biomimetic highly stretchable conductive dry adhesive patch according to example embodiments maintains a conformal contact with the skin of the human body during various movements such as wrist curl, thigh squat, writing, etc., and P, QRS and T curves which are clearly distinguished are observed. Thus, the biomimetic highly stretchable conductive dry adhesive patch according to example embodiments is also applicable when it is necessary to acquire biometric information in real time in daily life.

Although the application or utilization of the biomimetic highly stretchable conductive dry adhesive patch according to example embodiments is described based on the electrocardiogram measurement, the biomimetic highly stretchable conductive dry adhesive patch according to example embodiments may be used to measure various biological signals or to measure and collect electrical signals.

The above described embodiments may be widely applied to a flexible electronic product such as a wearable device, a bio-field, a diagnostic medical field, and a robotics field, and may be variously applied as a skin patch type wearable platform having electrical conductivity, adhesive properties and elasticity at the same time.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present inventive concept. Accordingly, all such modifications are intended to be included within the scope of the present inventive concept as defined in the claims. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A method of manufacturing a biomimetic highly stretchable conductive dry adhesive patch, the method comprising:
   providing a mold including a plurality of holes by etching a semiconductor substrate including an insulation layer based on a footing effect;
   providing a conductive polymer composite by dispersing mixed conductive fillers in a liquid elastomer, the mixed conductive fillers being formed by mixing one-dimensional conductive fillers and two-dimensional conductive fillers;
   applying the conductive polymer composite on the mold such that the conductive polymer composite is injected into the plurality of holes; and
   obtaining a conductive dry adhesive structure including a plurality of micropillars corresponding to the plurality of holes by performing a post-treatment on the conductive polymer composite applied on the mold and by removing the mold, wherein each of the plurality of micropillars includes:
a body portion; and
a tip portion having a spatula shape, formed on the body portion, and having an area larger than that of the body portion in a plan view,
wherein an amount of the one-dimensional conductive fillers included in the mixed conductive fillers is greater than an amount of the two-dimensional conductive fillers included in the mixed conductive fillers,
wherein a ratio of the one-dimensional conductive fillers and the two-dimensional conductive fillers in the mixed conductive fillers is within a range of about 8:2 to about 9.99:0.01,
wherein an aspect ratio obtained by dividing a height of each of the plurality of micropillars by a width of each of the plurality of micropillars is within a range of about 2 to about 4.

2. The method of claim 1, wherein an amount of the mixed conductive fillers dispersed in the liquid elastomer is less than or equal to about 1.0 weight percent (wt %) based on a total weight of the conductive polymer composite.

3. The method of claim 1, wherein:
each of the body portion and the tip portion has a cylindrical shape,
the body portion is formed on an elastic substrate including the conductive polymer composite, and has a first diameter and a first thickness, and
the tip portion is formed on the body portion, and has a second diameter larger than the first diameter and a second thickness smaller than the first thickness.

4. The method of claim 1, wherein each of the one-dimensional conductive fillers and the two-dimensional conductive fillers include a carbon-based nanoconductive material.

5. The method of claim 4, wherein the one-dimensional conductive fillers include a conductive material based on carbon nanotube (CNT).

6. The method of claim 4, wherein the two-dimensional conductive fillers include a conductive material based on a material selected from the group consisting of graphene, carbon black (CB) and graphite.

7. The method of claim 1, wherein the one-dimensional conductive fillers include a conductive material based on silver nanowire.

8. The method of claim 1, wherein the liquid elastomer includes a material selected from the group consisting of polydimethylsiloxane (PDMS), PDMS modified urethane acrylate (PUA), perfluoropolyether (PFPE) and polyethylene (PE).

9. The method of claim 1, wherein providing the mold includes:
forming a photoresist layer on the semiconductor substrate, the semiconductor substrate including a bare semiconductor wafer, the insulation layer formed on the bare semiconductor wafer, and a semiconductor layer formed on the insulation layer;
forming a photoresist pattern including a hole array by patterning the photoresist layer;
performing an etching process on the semiconductor layer using the photoresist pattern as a mask until the insulation layer is exposed;
removing the photoresist pattern; and
performing a surface treatment on the mold.

10. The method of claim 9, wherein each of the plurality of holes includes:
a first portion formed adjacent to the insulation layer, and having a shape corresponding to the tip portion; and
a second portion formed on the first portion, and having a shape corresponding to the body portion,
wherein a width and a thickness of the first portion are determined based on an execution time during which the etching process is performed on the semiconductor layer.

11. A biomimetic highly stretchable conductive dry adhesive patch, comprising:
an elastic structure formed of an elastic material, and including an elastic substrate and a plurality of micropillars formed on the elastic substrate; and
mixed conductive fillers formed by mixing one-dimensional conductive fillers and two-dimensional conductive fillers, and dispersed in the elastic structure to form a conductive network,
wherein each of the plurality of micropillars includes:
a body portion; and
a tip portion having a spatula shape, formed on the body portion, and having an area larger than that of the body portion in a plan view, and
wherein a conductive dry adhesive structure is formed by the elastic structure and the mixed conductive fillers,
wherein an amount of the one-dimensional conductive fillers included in the mixed conductive fillers is greater than an amount of the two-dimensional conductive fillers included in the mixed conductive fillers,
wherein a ratio of the one-dimensional conductive fillers and the two-dimensional conductive fillers in the mixed conductive fillers is within a range of about 8:2 to about 9.99:0.01,
wherein an aspect ratio obtained by dividing a height of each of the plurality of micropillars by a width of each of the plurality of micropillars is within a range of about 2 to about 4.

12. The biomimetic highly stretchable conductive dry adhesive patch of claim 11, wherein an amount of the mixed conductive fillers dispersed in the elastic structure is less than or equal to about 1.0 weight percent (wt %) based on a total weight of the elastic structure and the mixed conductive fillers.

13. The biomimetic highly stretchable conductive dry adhesive patch of claim 11, wherein:
each of the one-dimensional conductive fillers and the two-dimensional conductive fillers include a carbon-based nanoconductive material,
the one-dimensional conductive fillers include a conductive material based on carbon nanotube (CNT), and
the two-dimensional conductive fillers include a conductive material based on a material selected from the group consisting of graphene, carbon black (CB) and graphite.

14. A wearable device comprising:
a biomimetic highly stretchable conductive dry adhesive patch;
a measurer connected to the biomimetic highly stretchable conductive dry adhesive patch; and
a processor configured to perform a predetermined data processing operation based on an output of the measurer,
wherein the biomimetic highly stretchable conductive dry adhesive patch includes:
an elastic structure formed of an elastic material, and including an elastic substrate and a plurality of micropillars formed on the elastic substrate; and mixed conductive fillers formed by mixing one-dimensional conductive fillers and two-dimensional conductive fillers, and dispersed in the elastic structure to form a conductive network,
wherein each of the plurality of micropillars includes:
a body portion; and
a tip portion having a spatula shape, formed on the body portion, and having an area larger than that of the body portion in a plan view, and
wherein a conductive dry adhesive structure is formed by the elastic structure and the mixed conductive fillers,
wherein an amount of the one-dimensional conductive fillers included in the mixed conductive fillers is greater than an amount of the two-dimensional conductive fillers included in the mixed conductive fillers,
wherein a ratio of the one-dimensional conductive fillers and the two-dimensional conductive fillers in the mixed conductive fillers is within a range of about 8:2 to about 9.99:0.01,
wherein an aspect ratio obtained by dividing a height of each of the plurality of micropillars by a width of each of the plurality of micropillars is within a range of about 2 to about 4.

* * * * *